(12) United States Patent
Anastassiou et al.

(10) Patent No.: US 10,492,876 B2
(45) Date of Patent: Dec. 3, 2019

(54) DEVICES AND METHODS FOR LASER SURGERY

(71) Applicant: OmniGuide, Inc., Cambridge, MA (US)

(72) Inventors: Charalambos Anastassiou, Malden, MA (US); Vladimir Fuflyigin, Medford, MA (US); Marc Graham, Somerville, MA (US); Noam Josephy, Newton Center, MA (US); Thieu L. Le, Quincy, MA (US); Arnaz Singh Malhi, Watertown, MA (US); Robert Payne, Wellesley, MA (US); Lori Pressman, Cambridge, MA (US); Jesse Rusk, Malden, MA (US); Gil Shapira, Brookline, MA (US); Max Shurgalin, Lexington, MA (US); Crystal Simon, Boston, MA (US)

(73) Assignee: OmniGuide, Inc., Lexington, MA (US)

( * ) Notice: Subject to any disclaimer, the term of this patent is extended or adjusted under 35 U.S.C. 154(b) by 795 days.

(21) Appl. No.: 14/029,283

(22) Filed: Sep. 17, 2013

(65) Prior Publication Data
US 2014/0088577 A1    Mar. 27, 2014

Related U.S. Application Data

(60) Provisional application No. 61/787,242, filed on Mar. 15, 2013, provisional application No. 61/701,983, filed on Sep. 17, 2012.

(51) Int. Cl.
*A61B 34/00*    (2016.01)
*A61B 18/20*    (2006.01)
(Continued)

(52) U.S. Cl.
CPC ............ *A61B 34/76* (2016.02); *A61B 18/201* (2013.01); *A61B 18/22* (2013.01);
(Continued)

(58) Field of Classification Search
CPC .... A61N 2005/0632; A61N 2005/0633; A61B 1/008; A61B 1/00098; A61B 1/00128;
(Continued)

(56) References Cited

U.S. PATENT DOCUMENTS 3,865,113 A * 2/1975 Sharon .................. A61B 18/201
                                                         606/18
4,016,865 A    4/1977 Fredricks
(Continued)

FOREIGN PATENT DOCUMENTS

EP    1322214 B1    7/2003
EP    1367949 B1    12/2003
(Continued)

OTHER PUBLICATIONS

OmniGuide FlexGuide robotic flexible handpiece with straight entry, publicly released Jun. 10, 2011 (two sheets of illustrations).
(Continued)

*Primary Examiner* — Lynsey C Eiseman
*Assistant Examiner* — Jonathan T. Kuo
(74) *Attorney, Agent, or Firm* — Cozen O'Connor

(57) ABSTRACT

Small diameter tools are provided, and methods of use described, to facilitate less invasive surgical procedures employing laser beams. Such tools include distal tips that enhance the precise placement of optical waveguides, as well as enable cutting and dissecting procedures. A rotary coupler allows precise control of flexible conduits in which waveguides may be disposed. Waveguide tips with conical features protect waveguide ends and allow unobstructed propagation of the laser beam out of the waveguide. A
(Continued)

preferentially bending jacket for waveguides may be used to control an orientation of a waveguide disposed therein. Surgical waveguide assemblies may include various combinations of these components.

5 Claims, 41 Drawing Sheets

(51) Int. Cl.
  *A61B 18/00* (2006.01)
  *A61B 18/22* (2006.01)
  *A61B 90/00* (2016.01)
(52) U.S. Cl.
  CPC ............ *A61B 2018/0044* (2013.01); *A61B 2018/00339* (2013.01); *A61B 2018/00434* (2013.01); *A61B 2018/00577* (2013.01); *A61B 2018/00589* (2013.01); *A61B 2018/00601* (2013.01); *A61B 2018/00607* (2013.01); *A61B 2018/00642* (2013.01); *A61B 2018/2065* (2013.01); *A61B 2018/2238* (2013.01); *A61B 2018/2255* (2013.01); *A61B 2090/034* (2016.02); *A61B 2090/036* (2016.02); *A61B 2090/061* (2016.02); *A61B 2090/064* (2016.02)
(58) Field of Classification Search
  CPC .......... A61B 2017/00292; A61B 2017/00296; A61B 2017/00738; A61B 2017/320052; A61B 2017/320072; A61B 2018/00172; A61B 2018/2005; A61B 18/201; A61B 2018/2015; A61B 18/22; A61B 18/20; A61B 2090/037
  USPC .......... 607/17; 600/104, 108, 120, 129, 145, 600/146, 160, 164, 93.01, 100.02, 102.02
  See application file for complete search history.

(56) References Cited

U.S. PATENT DOCUMENTS

| | | | |
|---|---|---|---|
| 4,380,696 A * | 4/1983 | Masaki | B25J 19/023 219/124.34 |
| 4,652,083 A | 3/1987 | Laakmann | |
| 4,688,893 A | 8/1987 | Laakmann | |
| 4,911,712 A | 3/1990 | Harrington | |
| 4,917,083 A | 4/1990 | Harrington et al. | |
| 5,011,483 A | 4/1991 | Sleister | |
| 5,030,217 A | 7/1991 | Harrington | |
| 5,074,860 A | 12/1991 | Gregory et al. | |
| 5,136,676 A | 8/1992 | Arnett et al. | |
| 5,163,935 A | 11/1992 | Black et al. | |
| 5,209,747 A | 5/1993 | Knoepfler | |
| 5,217,453 A | 6/1993 | Wilk | |
| 5,243,399 A | 9/1993 | Koop et al. | |
| 5,261,905 A | 11/1993 | Doresey, III | |
| 5,261,906 A | 11/1993 | Pennino et al. | |
| 5,267,995 A | 12/1993 | Doiron et al. | |
| 5,292,320 A | 3/1994 | Brown et al. | |
| 5,312,398 A | 5/1994 | Hobart et al. | |
| 5,342,355 A * | 8/1994 | Long | A61B 18/245 606/15 |
| 5,368,015 A | 11/1994 | Wilk | |
| 5,395,030 A | 3/1995 | Kuramoto et al. | |
| 5,440,664 A | 8/1995 | Harrington et al. | |
| 5,454,807 A * | 10/1995 | Lennox | A61B 18/24 606/14 |
| 5,460,629 A | 10/1995 | Shlain et al. | |
| 5,496,308 A | 3/1996 | Brown et al. | |
| 5,509,916 A | 4/1996 | Taylor | |
| 5,567,471 A | 10/1996 | Harrington et al. | |
| 5,593,402 A | 1/1997 | Patrick | |
| 5,662,587 A | 9/1997 | Grundfest et al. | |
| 5,720,743 A | 2/1998 | Bischof et al. | |
| 5,738,679 A * | 4/1998 | Daikuzono | A61B 18/203 606/11 |
| 5,776,092 A | 7/1998 | Farin et al. | |
| 5,776,126 A | 7/1998 | Wilk et al. | |
| 5,833,684 A | 11/1998 | Franetzki | |
| 5,836,941 A | 11/1998 | Yoshihara et al. | |
| 5,872,879 A | 2/1999 | Hamm | |
| 5,893,828 A | 4/1999 | Uram | |
| 5,904,147 A | 5/1999 | Conlan et al. | |
| 5,964,780 A | 10/1999 | Balazs | |
| 6,013,997 A | 1/2000 | Heideman et al. | |
| 6,024,695 A | 2/2000 | Taylor et al. | |
| 6,139,543 A * | 10/2000 | Esch | A61B 18/26 606/15 |
| 6,258,083 B1 | 7/2001 | Daniel et al. | |
| 6,309,397 B1 | 10/2001 | Julian et al. | |
| 6,308,092 B1 * | 11/2001 | Hoyns | A61B 6/00 600/478 |
| 6,348,051 B1 | 2/2002 | Farin et al. | |
| 6,404,966 B1 | 6/2002 | Kawanishi et al. | |
| 6,463,200 B2 | 10/2002 | Fink et al. | |
| 6,471,643 B1 | 10/2002 | Henderson | |
| 6,603,911 B2 | 8/2003 | Fink et al. | |
| 6,743,239 B1 | 6/2004 | Kuehn et al. | |
| 6,770,081 B1 | 8/2004 | Cooper et al. | |
| 6,783,524 B2 | 8/2004 | Anderson et al. | |
| 6,802,838 B2 * | 10/2004 | Loeb | A61B 18/24 606/13 |
| 6,827,712 B2 | 12/2004 | Tovey et al. | |
| 6,890,332 B2 | 5/2005 | Truckai et al. | |
| 6,993,230 B2 | 1/2006 | Sanghera et al. | |
| 6,997,871 B2 | 2/2006 | Sonnenschein et al. | |
| RE39,152 E | 6/2006 | Aust et al. | |
| 7,083,571 B2 | 8/2006 | Wang et al. | |
| 7,167,622 B2 * | 1/2007 | Temelkuran | A61B 1/018 385/117 |
| 7,168,604 B2 | 1/2007 | Milliman et al. | |
| 7,204,844 B2 | 4/2007 | Jensen et al. | |
| 7,248,944 B2 | 7/2007 | Green | |
| 7,272,285 B2 | 9/2007 | Benoit et al. | |
| 7,311,962 B2 | 12/2007 | Fink et al. | |
| 7,315,675 B2 | 1/2008 | Harrington et al. | |
| 7,372,229 B2 | 5/2008 | Farritor et al. | |
| 7,435,216 B2 | 10/2008 | Kwon et al. | |
| 7,578,817 B2 | 8/2009 | Canady | |
| 7,691,120 B2 | 4/2010 | Shluzas et al. | |
| 7,748,979 B2 | 7/2010 | Nahlieli | |
| 7,785,422 B2 | 8/2010 | Autumn et al. | |
| 7,822,466 B2 | 10/2010 | Stoianovici et al. | |
| 7,858,049 B2 | 12/2010 | Smith et al. | |
| 7,922,718 B2 | 4/2011 | Moses et al. | |
| 7,927,272 B2 | 4/2011 | Bayer et al. | |
| 8,038,670 B2 | 10/2011 | McClurken | |
| 8,048,070 B2 | 11/2011 | O'Brien et al. | |
| 8,120,301 B2 | 2/2012 | Goldberg et al. | |
| 8,162,973 B2 | 4/2012 | Cunningham | |
| 8,190,238 B2 | 5/2012 | Moll et al. | |
| 2004/0199148 A1 | 10/2004 | Haan et al. | |
| 2004/0243147 A1 | 12/2004 | Lipow | |
| 2005/0171520 A1 * | 8/2005 | Farr | A61B 18/245 606/15 |
| 2006/0004398 A1 * | 1/2006 | Binder, Jr. | A61B 17/3417 606/191 |
| 2007/0021738 A1 | 1/2007 | Hasser et al. | |
| 2007/0049928 A1 | 3/2007 | Fleenor et al. | |
| 2007/0053640 A1 | 3/2007 | Goell et al. | |
| 2007/0185474 A1 | 8/2007 | Nahen | |
| 2007/0239153 A1 | 10/2007 | Hodorek et al. | |
| 2007/0270788 A1 | 11/2007 | Nahen et al. | |
| 2008/0004634 A1 | 1/2008 | Farritor et al. | |
| 2008/0116184 A1 | 5/2008 | Fredrick et al. | |
| 2008/0167674 A1 | 7/2008 | Bodduluri et al. | |
| 2008/0221591 A1 | 9/2008 | Farritor et al. | |
| 2008/0269557 A1 | 10/2008 | Marescaux et al. | |
| 2008/0287933 A1 | 11/2008 | Pini | |
| 2009/0003975 A1 | 1/2009 | Kuduvalli et al. | |
| 2009/0088772 A1 | 4/2009 | Blumenkranz | |
| 2009/0088775 A1 | 4/2009 | Swarup et al. | |

(56) References Cited

U.S. PATENT DOCUMENTS

| | | |
|---|---|---|
| 2009/0171332 A1 | 7/2009 | Bonneau |
| 2009/0209973 A1 | 8/2009 | East |
| 2009/0248041 A1 | 10/2009 | Williams et al. |
| 2009/0275927 A1 | 11/2009 | Fein et al. |
| 2009/0281536 A1 | 11/2009 | Beckman et al. |
| 2010/0076381 A1 | 3/2010 | Simonsen |
| 2010/0082042 A1 | 4/2010 | Drews |
| 2010/0100085 A1 | 4/2010 | Lewinsky et al. |
| 2010/0168586 A1 | 7/2010 | Hillman et al. |
| 2010/0179525 A1 | 7/2010 | Neuberger |
| 2010/0204713 A1 | 8/2010 | Ruiz Morales |
| 2010/0204721 A1 | 8/2010 | Young et al. |
| 2010/0286791 A1 | 11/2010 | Goldsmith |
| 2010/0331856 A1 | 12/2010 | Carlson et al. |
| 2011/0060321 A1 | 3/2011 | Chandler et al. |
| 2011/0087202 A1 | 4/2011 | Lewinsky et al. |
| 2011/0144659 A1 | 6/2011 | Sholev |
| 2011/0160535 A1 | 6/2011 | Bayer et al. |
| 2011/0190749 A1 | 8/2011 | McMillan et al. |
| 2011/0190782 A1 | 8/2011 | Fleming et al. |
| 2011/0196199 A1 | 8/2011 | Donhowe et al. |
| 2011/0208007 A1 | 8/2011 | Shohat et al. |
| 2011/0224688 A1 | 9/2011 | Larkin et al. |
| 2011/0238080 A1 | 9/2011 | Ranjit et al. |
| 2012/0016362 A1 | 1/2012 | Heinrich et al. |
| 2012/0136372 A1 | 5/2012 | Amat Girbau et al. |
| 2014/0324034 A1* | 10/2014 | Assaf ............... A61B 18/22 606/10 |

FOREIGN PATENT DOCUMENTS

| | | |
|---|---|---|
| EP | 1496805 B1 | 1/2005 |
| EP | 2011440 A1 | 1/2009 |
| EP | 2298222 A2 | 3/2011 |
| EP | 2397101 A2 | 12/2011 |
| EP | 2428157 A1 | 3/2012 |
| EP | 2433585 A1 | 3/2012 |
| WO | WO-1996032052 A1 | 10/1996 |
| WO | WO-2001097694 A1 | 12/2001 |
| WO | WO-2007130382 A2 | 11/2007 |
| WO | WO-2008014425 A2 | 1/2008 |
| WO | WO-2008101228 A2 | 8/2008 |
| WO | WO-2009037945 A1 | 3/2009 |
| WO | WO-2010098871 A2 | 9/2010 |
| WO | WO-2010122563 A1 | 10/2010 |
| WO | WO-2011051253 A1 | 5/2011 |
| WO | WO-2011075442 A1 | 6/2011 |
| WO | WO-2011115387 A2 | 9/2011 |
| WO | WO-2011143338 A1 | 11/2011 |
| WO | WO-2011147651 A1 | 12/2011 |
| WO | WO-2011156733 A2 | 12/2011 |
| WO | WO-2011161626 A2 | 12/2011 |
| WO | WO-2013068978 A1 | 5/2013 |

OTHER PUBLICATIONS

Knight, J.C., et al., "Photonic Band Gap Guidance in Optical Fibers", Science, Nov. 20, 1998, vol. 282, pp. 1476-1478.

Temelkuran, B., et al., "Wavelength-scalable hollow optical fibres with large photonic bandgaps for $CO_2$ laser transmission" Nature 420, pp. 650-653, 2002.

U.S. Appl. No. 61/558,521, Gelstein.

U.S. Appl. No. 61/567,840, Kendrick.

* cited by examiner

FIG. 1Eα

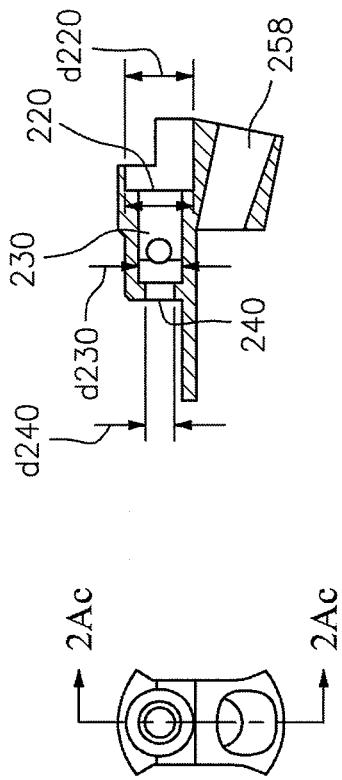
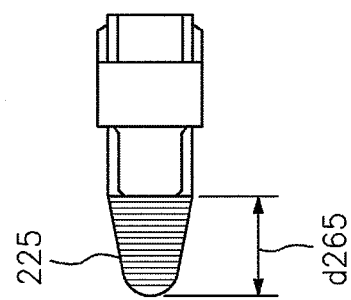
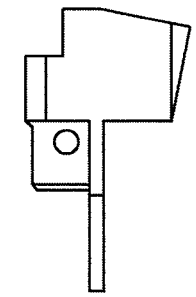
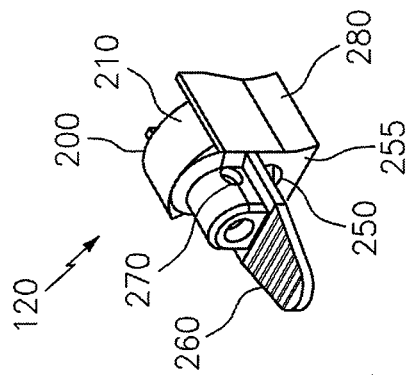
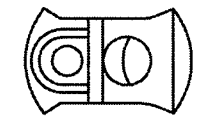
FIG. 2Ac
FIG. 2Ab
FIG. 2Ad
FIG. 2Aa
FIG. 2Ae
FIG. 2Af

FIG. 2Cα

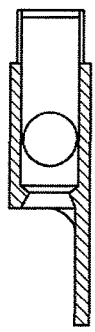
FIG. 3A
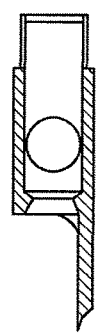
FIG. 3B
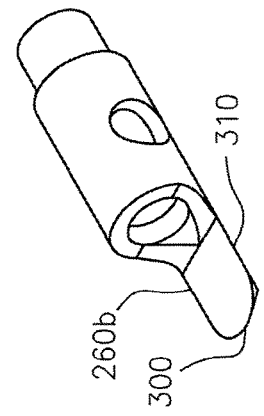
FIG. 3A1
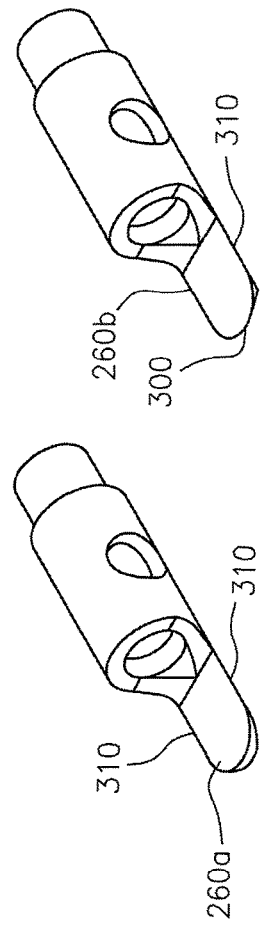
FIG. 3B1
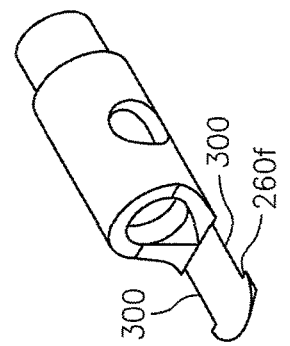
FIG. 3A2
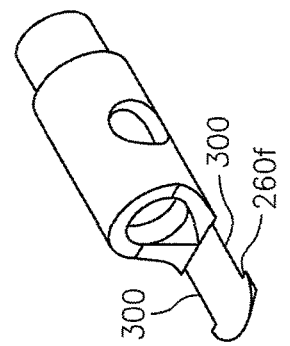
FIG. 3A3
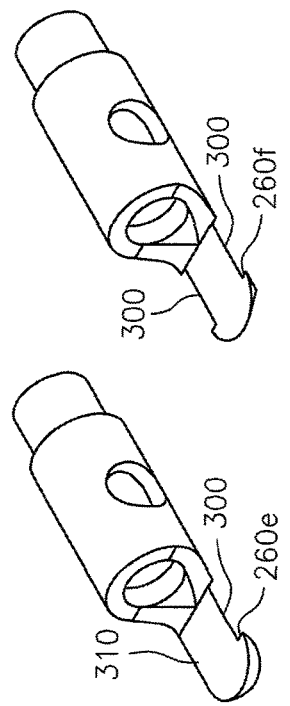
FIG. 3A4
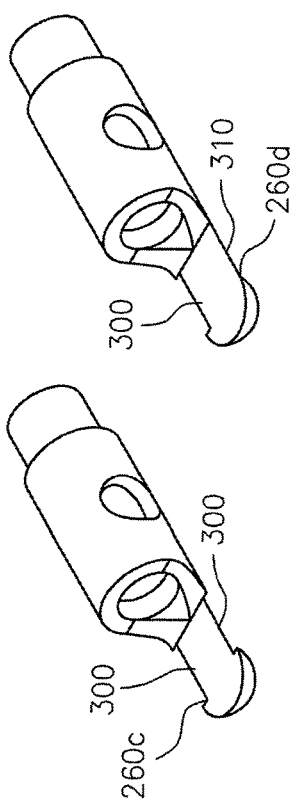
FIG. 3B2

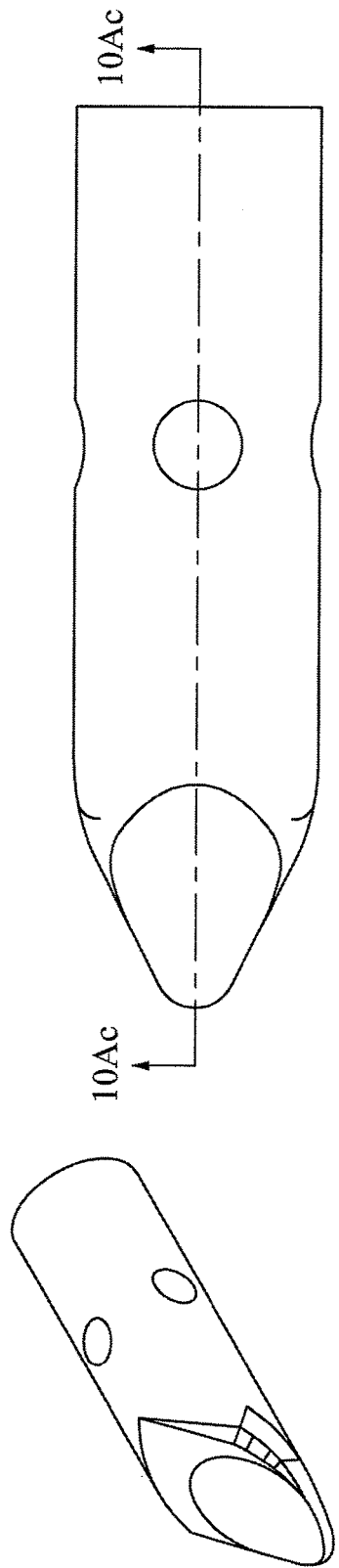
FIG. 10Ab
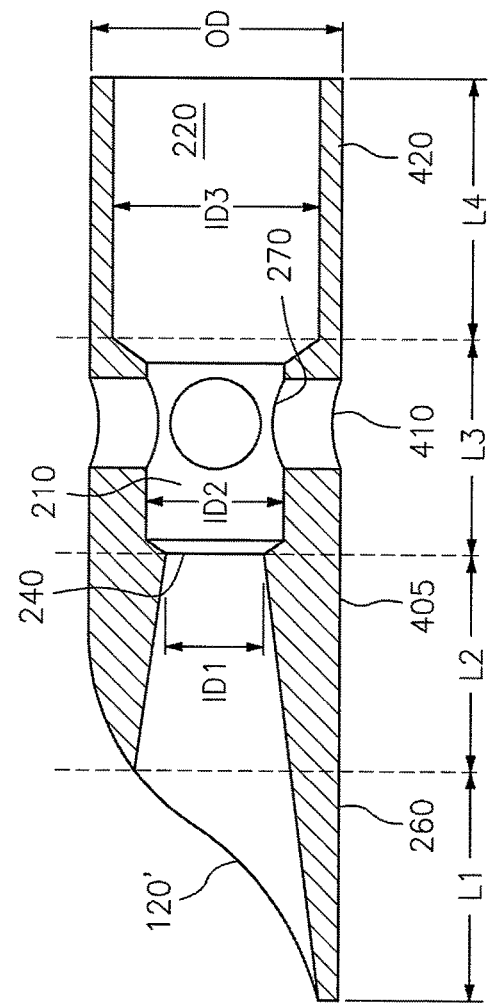
FIG. 10Aa
FIG. 10Ac

FIG. 18B
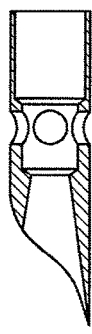
FIG. 18A
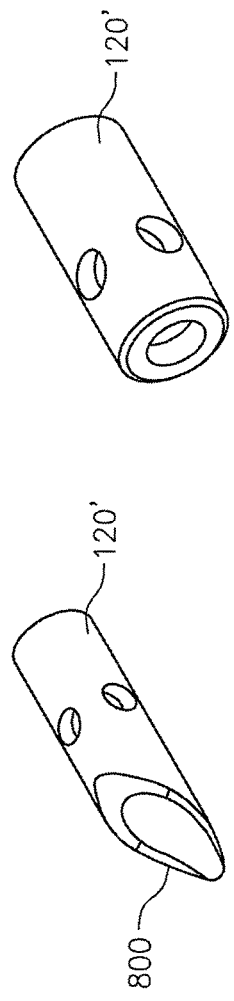
FIG. 18B1
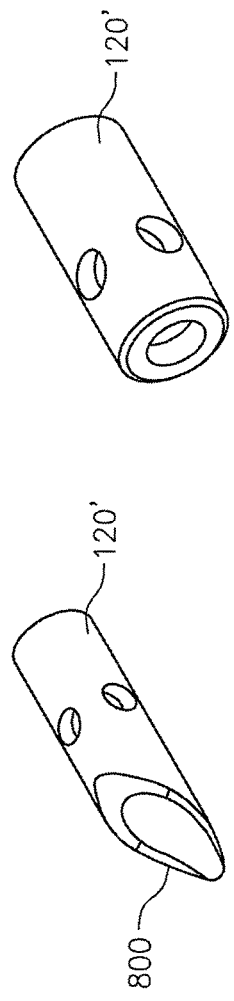
FIG. 18A1
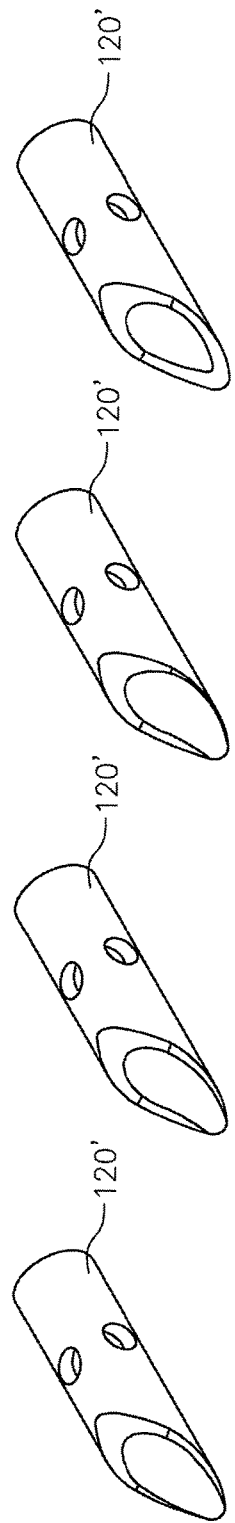
FIG. 18A5
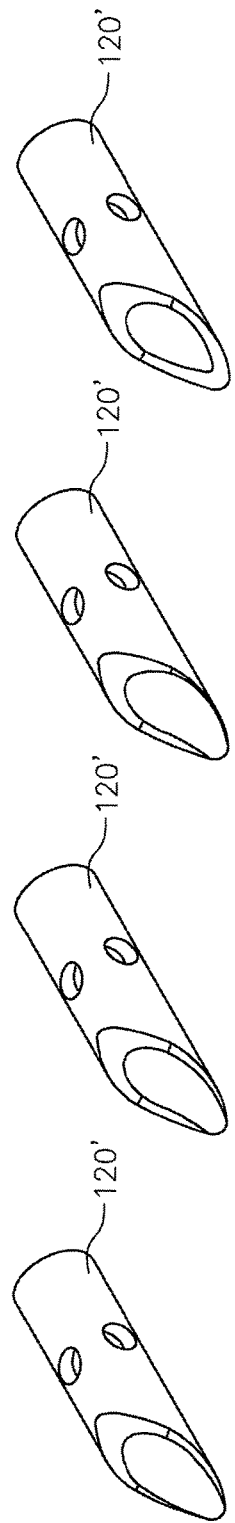
FIG. 18A4
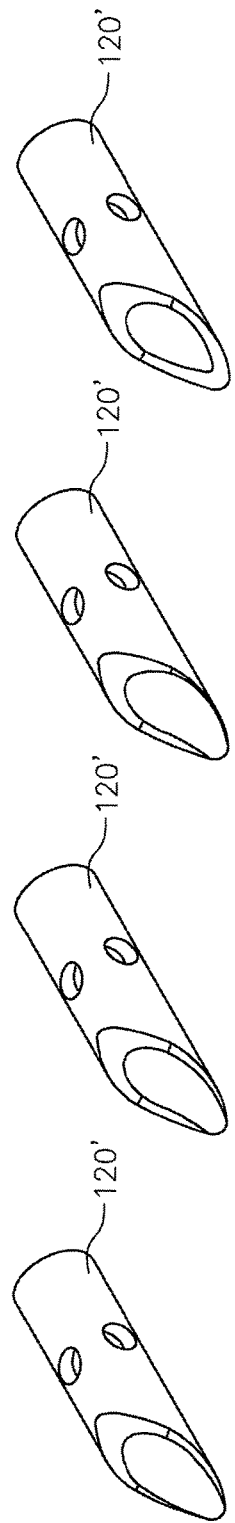
FIG. 18A3
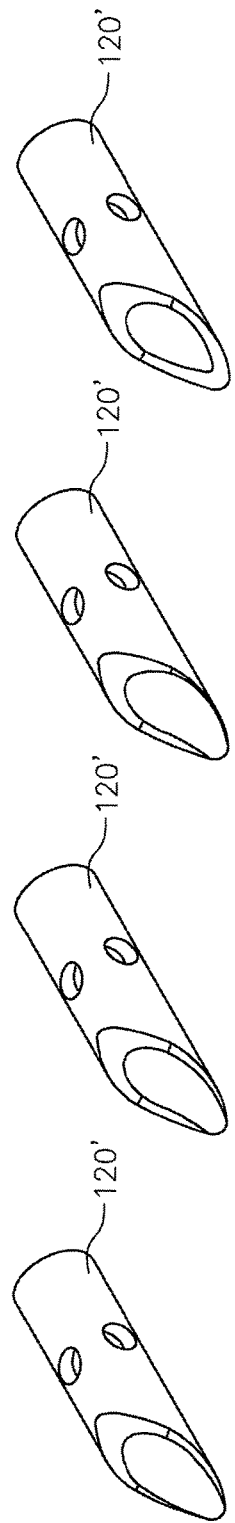
FIG. 18A2

DEVICES AND METHODS FOR LASER SURGERY

RELATED APPLICATIONS

This application claims the benefit of priority under 35 U.S.C. § 119(e) to U.S. Provisional Patent Application Ser. No. 61/701,983 filed Sep. 17, 2012, and U.S. Provisional Patent Application Ser. No. 61/787,242 filed Mar. 15, 2013. Each of these applications is incorporated herein by reference in its entirety.

FIELD OF THE INVENTION

The present invention relates to medical lasers, particularly for components of medical laser systems.

BACKGROUND

There is a trend toward less invasive surgical procedures done by introducing small diameter, flexible tools into natural body openings and small incisions. These tools can enable tissue visualization, imaging, analysis, manipulation, cutting, coagulation, and removal. An example of a procedure done through a natural body opening is polyp visualization and removal during a colonoscopy. Examples of procedures done through one or more small incisions include laparoscopic myomectomy, hysterectomy or cholecystectomy. See for example "Robot-assisted laparoscopic myomectomy and adenomyomectomy with a flexible $CO_2$ laser device" *Journal of Robotic Surgery*, June 2013, Volume 7, Issue 2, pp 157-162. Laparoscopic incisions are typically 3 mm-15 mm. Some procedures can be done through incisions 3 mm or smaller, and have been called "needlescopic." See for example "Reevaluation of needlescopic surgery", *Surgical Endoscopy*, Jul. 26, 2011, and "New Trends in Minimally Invasive Urological Surgery", *International Brazilian Journal of Urology*, Vol 35 (4) pp 514-520.

A type of laparoscopic surgery is single incision laparoscopic surgery, where a multiport trocar is used to introduce a cluster of surgical tools. Incisions that start from an instrument already in a natural body opening, called natural orifice translumenal endoscopic surgery, or "NOTES" are a topic of current surgical research, as are various percutaneous procedures. Examples include NOTES cholecystectomy [Rolanda C, Lima E, Pêgo J M, et al. (January 2007), "Third-generation cholecystectomy by natural orifices: transgastric and transvesical combined approach (with video)" *Gastrointestinal Endoscopy* 65 (1): 111-7], and nephrectomy [Sánchez-Margallo F M, Asencio J M, Tejonero M C, et al. (2008), "Technical feasibility of totally natural orifice cholecystectomy in a swine model," *Minimally Invasive Therapy & Allied Technologies* 17 (6): 361-4)].

A small diameter flexible tool can be beneficial for such procedures. To access regions that are not necessarily close to the point of tool introduction, longer tools may also be desirable.

Long, thin, flexible waveguides are generally well adapted for performing the procedures described above, and suit the current growing interest in and use of laser surgery. For example solid core silica fibers are used to guide wavelength of KPT (532 nm), Nd:YAG (1.06 μm), Ho:YAG (2.1 μm) and Tm:YAG (2 μm) lasers widely used in medical applications. For $CO_2$ laser beams (approximately 10.6 μm wavelength), hollow waveguides may be useful, as the $CO_2$ wavelength is generally highly absorbed in materials traditionally used for optical fibers, such as silicates and thermoplastic polymers. Hollow waveguides may be made of metal (see, e.g., U.S. Pat. Nos. 4,652,083 and 4,688,893, assigned to Laakman Electro-Optics, Inc.) or metalized tubes (see, e.g., U.S. Pat. Nos. 5,440,664, 5,567,471, and 7,315,675 to Harrington et al., assigned to Rutgers, The State University of New Jersey), in which the metal mirror guides the optical radiation.

Flexible hollow waveguides may also be made by drawing structured thermoplastic preforms. One example of such a structure is described in U.S. Pat. Nos. 6,463,200 and 6,603,911 to Fink et al., assigned to Massachusetts Institute of Technology, in which a dielectric stack of materials having different refractive indices is arranged in concentric cylinders about the waveguide axis thus providing the mirror structure that guides the radiation. Flexible hollow waveguides drawn from structured thermoplastic preforms are also disclosed in U.S. Pat. No. 7,311,962 to Fink et al. and U.S. Pat. No. 7,272,285 to Benoit et al., both assigned to Massachusetts Institute of Technology. See also "Wavelength-scalable hollow optical fibres with large photonic bandgaps for $CO_2$ laser transmission" Temelkuran, et al *Nature* 420, 650 (2002); U.S. Pat. Nos. 6,404,966 and 6,993,230; and Knight et al., "Photonic Band Gap Guidance in Optical Fibers," *Science* 282, 1476 (1998), which describe a further preform structure for drawing flexible hollow waveguides For mechanical strength and/or ease of manipulation, it may be desirable to place waveguides inside other mechanical structures that provide protection, a preferred bend plane, strength, and/or a place onto which other structures, such as handles or tips can be affixed.

One example of such a mechanical structure is a jacket. In some cases the cladding, e.g., support layer 150 in FIG. 1A or monolithic support cladding 270 of FIG. 2D of U.S. Pat. No. 7,272,285 serves as the jacket. In this case, because of the way the waveguide is manufactured, the jacket and waveguide are one piece.

A jacket may also be put on the waveguide after the waveguide is manufactured. Suitable jacket materials include plastic materials, such as polyesters (e.g., Hytrel® thermoplastic plastic elastomer), polyamides (e.g., nylon), polyether block amides (e.g., Pebax®), polyether ketones (e.g., "PEEK"), polyether sulphones, polyether imides (e.g., Ultem®), polyimides (e.g., Kapton®, Vespel®), polyethylenes, and/or polyurethanes. The jacket may also be made of whole metal tubing or wholly from braided, twisted, or coiled metal wires. The jacket may also be made of glass (e.g., silica glass).

Jackets made of optically suitable materials (e.g., optical quality polymer of silica glass) can also perform an optical function of guiding additional wavelength for illumination, aiming or collecting optical signal.

Another example of such a mechanical structure is a conduit. Conduits are typically placed on waveguides or waveguide assemblies after manufacturing or assembly. Conduits can be either flexible or rigid, or have a rigid portion and a flexible portion. A conduit can have multiple functions: coupling a waveguide with an external manipulator (e.g., a human hand, handpiece, electromechanical actuator or robotic device); mechanical protection of waveguide, control of waveguide bending and associated optical performance variation (optical loss due to bends); keeping the inserted waveguide in place and optically aligned with distal tips; mechanical support of other features that may be affixed to the conduit (e.g., distal tips, suction irrigation tools). The conduit is preferably sterilizable and steerable, has a small diameter, and may be disposable, or reusable. Suitable materials for conduits include stainless steel (e.g., 300 and 400 series surgical grade steels), titanium, and polymer materials (e.g., silicones, polyamides, polycarbonates, PEEK, and polyolefin).

Waveguides or waveguide conduits are likely to be used in conjunction with trocar devices. The trocar not only protects the incision site from damage, such as abrasion or tearing that can occur when instruments are introduced or translated repeatedly through a single site, they can also help stabilize the tool. For a discussion on the importance of tool stabilization, see, for example, "Active tremor cancellation by a "Smart" handheld vitreoretinal microsurgical tool using swept source optical coherence tomography" 8 Oct. 2012/ Vol. 20, No. 21/OPTICS EXPRESS 23414.

At times, certain surgical uses of optical waveguides may result in tissue debris, fluid, or smoke being deposited, or landing on the portion close to the patient. Such tissue debris may absorb laser energy, including backscattered laser energy and heat the waveguide. Such tissue debris, may impede or slow normal passive cooling resulting from thermal dissipation, and/or more active cooling resulting from fluid, including gas flow through the waveguide core. The combination of increased heating and reduced cooling may overheat and thus damage the waveguide.

Thus, there is a need to protect the portion of the waveguide close to the surgical site. One approach is to flow fluid through hollow core waveguides. Gas flow may be used for clearing tissue debris and blood during tissue cutting, for cooling the waveguide and for therapeutic reasons such as assisting tissue coagulation. The gas flowing out of the waveguide may also assist in keeping the waveguide core from clogging and from damage due to the splattering, splashing, or deposition of tissue debris, including smoke and fluids. Protection of the waveguide distal end may also be achieved by a tip attached to the waveguide distal end. See, e.g., U.S. Pat. No. 7,167,622, incorporated herein by reference in its entirety.

As with non-laparoscopic surgical tools, the portion of the tool that interacts with the tissue being treated is important. There is a need for tools that provide the ability to aim the treatment precisely in space, including in x- and y-directions, or parallel to the tissue surface, and in z-direction, or perpendicular to the tissue surface, haptic feedback, and an ability to select, and vary particular surgical tasks, such as performing blunt dissection, imaging, analyzing, cutting, coagulating, ablating, and removing tissue.

SUMMARY

For some applications, it may be desirable to use a distal tip that is coupled to a waveguide either by being attached to a waveguide conduit, or directly to a jacket or waveguide, with the distal tip providing additional functionality. For example, distal tips may facilitate the manipulation of tissue. There is also a need for a tip that may allow tactile, audible or force or/and distance, as well as visible feedback during surgical procedures. A surgeon or a machine interface may use such feedback to adjust the position of the tip and waveguide. The distal tips disclosed herein may indicate the position of where laser radiation, not visible to the naked eye, strikes the tissue.

Distal tips may or may not themselves be waveguides. There is a need for tips that help the surgeon maintain a constant spot size and/or help the surgeon select a spot size. In some applications, it may be desirable to have distal tips that change the shape of the spot as it interacts with the tissue. For example, in certain circumstances, it may be desirable to clip, filter, or shape the spot, so the relative variation in power over the spot is reduced, or so the overall shape is modified.

Distal tips that are aligned with respect to the axis of the waveguide may be advantageous. Moreover, distal tips may preferably be engineered so as to take up a small portion of the field of view. Distal tips may be adapted for grasping by a robot or manual grasper.

In an aspect, embodiments of the invention include a distal tip for coupling to a waveguide. The distal tip includes a frame defining an (i) inlet for receiving the waveguide therethrough; and (ii) an outlet aligned with the inlet adapted for (1) permitting egress of radiation from an output end of the waveguide and (2) abutting an end face of the waveguide, the outlet having a smaller diameter than a diameter of the inlet. The frame (a) comprises a single piece of material, or (b) is transparent, or (c) defines at least one through hole proximate the inlet configured to enable visualization of a position of the waveguide, or (d) further defines a rectangular handle adapted to mate with a manipulator and configured to be grasped by the manipulator on any of three sides, or combinations thereof.

One or more of the following features may also be included. The frame may define an interface for coupling with a waveguide conduit, the interface being disposed upstream of the waveguide inlet. The interface may define an opening having a larger diameter than a diameter of the inlet.

The frame may further define a cantilevered distal end portion. The cantilevered distal end portion may have a sharp edge suitable for cutting tissue, the sharp edge having a thickness of, e.g., less than 0.4 mm. The cantilevered distal end portion may have a blunt edge suitable for dissecting tissue, the blunt edge having a thickness of e.g., greater than 0.4 mm.

The cantilevered distal end portion may include at least one of a contour and indicia indicator configured to indicate a laser beam path exiting the outlet. The cantilevered distal end portion may be interfaced to at least one of a force or a distance feedback sensor adapted to provide feedback to at least one of a robot or a computer interface. The cantilevered distal end portion may include a backstop.

The outlet may define an angled end portion. The angled end portion may include a sidewall of varying thickness. The frame may further include a handle adapted to mate with a manipulator.

A waveguide may be coupled to the distal tip, with an aperture of the outlet being greater than or equal to a numerical aperture of the waveguide.

A conical feature may be defined between the inlet and outlet.

In an aspect, embodiments of the invention include a distal tip for coupling to a waveguide. The distal tip includes a frame defining an (i) inlet for receiving the waveguide therethrough; and (ii) an outlet aligned with the inlet adapted for (1) permitting egress of radiation from an output end of the waveguide and (2) abutting an end face of the waveguide, the outlet having a smaller diameter than a diameter of the inlet; and (iii) a cantilevered distal end portion. The cantilevered distal end portion comprises (a) at least one of a contour and an indicia indicator configured to indicate a laser beam path exiting the outlet, or (b) markings configured to provide a visual reference for assessing at least one of a depth of an incision in target tissue or dimensions of the target tissue, or (c) a sharp edge suitable for cutting tissue and a blunt edge suitable for dissecting tissue, or (d) combinations thereof.

One or more of the following features may also be included. The frame may define an interface for coupling with a waveguide conduit, the interface being disposed upstream of the waveguide inlet. The interface may define an opening having a larger diameter than a diameter of the inlet.

The cantilevered distal end portion may have a sharp edge suitable for cutting tissue, the sharp edge having a thickness of, e.g., less than 0.4 mm. The cantilevered distal end portion may have a blunt edge suitable for dissecting tissue, the blunt edge having a thickness of e.g., greater than 0.4 mm.

The cantilevered distal end portion may include a backstop.

The outlet may define an angled end portion. The angled end portion may include a sidewall of varying thickness. The frame may further include a handle adapted to mate with a manipulator.

A waveguide may be coupled to the distal tip, with an aperture of the outlet being greater than or equal to a numerical aperture of the waveguide.

A conical feature may be defined between the inlet and outlet.

In yet another aspect, embodiments of the invention include a surgical waveguide assembly that includes a conduit for a waveguide, and a distal tip disposed on a distal end of the conduit. The distal tip includes a frame defining (i) an inlet for receiving the waveguide therethrough; and (ii) an outlet aligned with the inlet adapted for (1) permitting egress of radiation from an output end of the waveguide and (2) abutting an end face of the waveguide, the outlet having a smaller diameter than a diameter of the inlet. The distal tip is permanently attached to a distal end of the conduit.

One or more of the following features may be included. The distal tip may be permanently attached to the distal end of the conduit by at least one of gluing, brazing, welding, and soldering.

The frame may (a) comprise a single piece of material, (b) be transparent, (c) further define a cantilevered distal end portion comprising at least one of a contour and an indicia indicator configured to indicate a laser beam path exiting the outlet, (d) further define a cantilevered distal end portion comprising markings configured to provide a visual reference for assessing at least one of a depth of an incision in target tissue or dimensions of the target tissue, or (e) further define a cantilevered distal end portion comprising sharp edge suitable for cutting tissue and a blunt edge suitable for dissecting tissue.

In another aspect, embodiments of the invention include a waveguide conduit including an elongated hollow structure configured to receive a waveguide. An end portion of the structure defines (i) an inlet for receiving the waveguide therethrough; and (ii) an outlet aligned with the inlet adapted for (1) permitting egress of radiation from an output end of the waveguide and (2) abutting an end face of the waveguide, the outlet having a smaller diameter than a diameter of the inlet. The structure may further define a cantilevered distal end portion.

One or more of the following features may also be included. The waveguide may be disposed in the conduit. The conduit may include a gripping portion and a cannula portion.

In still another aspect, embodiments of the invention include a surgical waveguide assembly including a waveguide and a distal tip permanently attached to the waveguide. The distal tip includes a frame defining (i) an inlet for receiving the waveguide therethrough; and (ii) an outlet aligned with the inlet adapted for (1) permitting egress of radiation from an output end of the waveguide and (2) abutting an end face of the waveguide, the outlet having a smaller diameter than a diameter of the inlet.

In still another aspect, embodiments of the invention include a surgical waveguide assembly including a waveguide disposed in a jacket, and a distal tip permanently attached to the jacket. The distal tip includes a frame defining (i) an inlet for receiving the waveguide therethrough; and (ii) an outlet aligned with the inlet adapted for (1) permitting egress of radiation from an output end of the waveguide and (2) abutting an end face of the waveguide, the outlet having a smaller diameter than a diameter of the inlet.

In another aspect, embodiments of the invention include a laser radiation delivery system including a flexible conduit; a distal tip disposed on a distal end of the flexible conduit; and a locking mechanism disposed on a proximal end of the flexible conduit. The distal tip is configured to block movement of at least one of a waveguide or a waveguide assembly in the conduit beyond the distal tip and (ii) the locking mechanism is configured to restrain the waveguide or waveguide assembly.

In another aspect, embodiments of the invention include a waveguide conduit including an elongated hollow structure configured to receive a waveguide, an end portion of the structure defining (i) an inlet for receiving the waveguide therethrough; and (ii) an outlet aligned with the inlet adapted for (1) permitting egress of radiation from an output end of the waveguide and (2) abutting an end face of the waveguide, the outlet having a smaller diameter than a diameter of the inlet. The structure may further define a cantilevered distal end portion.

In another aspect, embodiments of the invention include a method for treating a patient with a laser beam. A distal end of a waveguide disposed in a flexible conduit is introduced into the patient through a trocar. A distal tip disposed at the distal end of the flexible conduit may be grasped with a manipulator tool. The distal tip has a handle adapted to mate with the manipulator. Tissue of the patient may be manipulated with a cantilevered distal end portion of the distal tip. An end of the waveguide may be positioned a predetermined stand-off distance from a portion of the tissue to be treated with the laser beam, the predetermined stand-off distance being defined by a length of the cantilevered distal end portion of the distal tip. The laser beam may be aimed at target tissue using the cantilevered end of the distal tip to position the laser beam.

One or more of the following features may be included. Manipulating tissue may include at least one of blunt dissection and cutting. A length of the cantilevered distal end portion of the distal tip may be adjusted, thereby adjusting the predetermined stand-off distance for tissue treatment. The length may be adjusted manually, or may be adjusted by a computer-controlled interface or by a mechanical manipulator. The cantilevered distal end portion of the distal tip may include a backstop, and the backstop may be inserted behind a layer of tissue being treated with the laser beam. Markings on the distal tip may be used to assess at least one of a depth of an incision in the target tissue or dimensions of the target tissue.

The distal tip may have a cross section adapted to facilitate grasping or mating with a tool, for example flat edges, such as a hexagonal or rectangular cross section suitable for fitting into an open female socket, of matching design, i.e., hexagonal or rectangular.

In yet another aspect, embodiments of the invention include a method for treating a patient with a laser beam, including introducing a distal end of a waveguide disposed in a flexible conduit into the patient through a trocar. A distal tip disposed at the distal end of the flexible conduit is grasped with a manipulator tool, the distal tip having a handle adapted to mate with the manipulator. A length of a cantilevered distal end portion of the distal tip is adjusted, thereby adjusting a predetermined stand-off distance for tissue treatment, the predetermined stand-off distance being defined by a length of the cantilevered distal end portion of the distal tip. Tissue of the patient is manipulated with the cantilevered distal end portion of the distal tip.

One or more of the following features may be included. The length may be adjusted manually, by a computer-controlled interface or by a mechanical manipulator. Manipulating tissue may include at least one of blunt dissection and cutting. The cantilevered distal end portion of the distal tip may include a backstop, and the backstop may be inserted behind a layer of tissue being treated with the laser beam.

In another aspect, embodiments of the invention include a method for treating a patient with a laser beam, including introducing a distal end of a waveguide disposed in a flexible conduit into the patient through a trocar. A distal tip disposed at the distal end of the flexible conduit is grasped with a manipulator tool, the distal tip having a handle adapted to mate with the manipulator. Markings on the distal tip are used to assess at least one of a depth of an incision in the target tissue or dimensions of the target tissue.

In another aspect, embodiments of the invention include a method for treating a patient with a laser beam. The method includes (i) introducing a distal end of a waveguide disposed in a rigid handpiece into the patient, a distal tip being disposed at a distal end of the rigid handpiece; and (ii) manipulating tissue of the patient with a cantilevered distal end portion of the distal tip.

One or more of the following features may be included. Manipulating tissue may include at least one of blunt dissection and cutting. An end of the waveguide may be positioned a predetermined stand-off distance from a portion of the tissue to be treated with the laser beam, the predetermined stand-off distance being defined by a length of the cantilevered distal end portion of the distal tip.

The laser beam may be aimed at target tissue using the cantilevered distal end of the distal tip to position the laser beam.

A length of the cantilevered distal end portion of the distal tip may be adjusted, thereby adjusting the predetermined stand-off distance for tissue treatment. The length may be adjusted manually and/or by a computer-controlled interface.

The cantilevered distal end portion of the distal tip may include a backstop, and the backstop may be inserted behind a layer of tissue being treated with the laser beam. Markings on the distal tip may be used to assess at least one of a depth of an incision in the target tissue or dimensions of the target tissue.

In yet another aspect, embodiments of the invention include a method for manufacturing a surgical waveguide assembly. The method includes providing a rigid handpiece, and attaching a distal tip to the rigid handpiece. The distal tip includes a frame defining (i) an inlet for receiving the waveguide therethrough; and (ii) an outlet aligned with the inlet adapted for (1) permitting egress of radiation from an output end of the waveguide and (2) abutting an end face of the waveguide, the outlet having a smaller diameter than a diameter of the inlet. A waveguide may be inserted into the rigid handpiece.

In another aspect, embodiments of the invention include a method for manufacturing a surgical waveguide assembly. The method includes providing a flexible conduit; and permanently attaching a distal tip to the flexible conduit. The distal tip includes a frame defining (i) an inlet for receiving the waveguide therethrough; (ii) an outlet aligned with the inlet adapted for (1) permitting egress of radiation from an output end of the waveguide and (2) abutting an end face of the waveguide, the outlet having a smaller diameter than a diameter of the inlet; and (iii) a handle adapted to mate with a manipulator. A waveguide may be inserted into the flexible conduit. The distal tip may be permanently attached to the conduit by at least one of gluing, brazing, welding, or soldering.

In still another aspect, embodiments of the invention include a method for manufacturing a waveguide conduit. The method includes providing an elongated hollow structure configured to receive a waveguide. A distal end portion of the structure is shaped to define (i) an inlet for receiving the waveguide therethrough; and (ii) an outlet aligned with the inlet adapted for (1) permitting egress of radiation from an output end of the waveguide and (2) abutting an end face of the waveguide, the outlet having a smaller diameter than a diameter of the inlet. Shaping may include at least one of machining, forming, and adding material.

In another aspect, embodiments of the invention include a method for manufacturing a surgical waveguide assembly. The method includes providing a waveguide jacket; and attaching a distal tip to the waveguide jacket. The distal tip includes a frame defining (i) an inlet for receiving the waveguide therethrough; (ii) an outlet aligned with the inlet adapted for (1) permitting egress of radiation from an output end of the waveguide and (2) abutting an end face of the waveguide, the outlet having a smaller diameter than a diameter of the inlet; and (iii) a handle adapted to mate with a manipulator. A waveguide may be inserted into the jacket.

In an aspect, an embodiment of the invention may include a laser radiation delivery system including a rotary coupler; a flexible conduit attached to a first end of the rotary coupler; and a distal tip disposed on a distal end of the flexible conduit.

One or more of the following features may be included. A waveguide may be coupled to a second end of the rotary coupler. The waveguide may pass through the rotary coupler.

In another aspect, embodiments of the invention may include a rotary coupler for coupling a waveguide assembly. The rotary coupler may include a waveguide portion including a waveguide retention member; and a conduit portion adapted for coupling with the waveguide portion and for rotation relative thereto.

One or more of the following features may be included. The conduit portion may include a rotational end cap. The waveguide portion may include at least one of a rotational end cap, a ball bearing, and a spindle lock nut. The waveguide portion may include a bearing housing adapted to be connected to a waveguide assembly, e.g., with a locking nut. The waveguide retention member may include an annular gripper adapted to be disposed within the bearing housing.

In another aspect, embodiments of the invention include a waveguide assembly including a cylindrical jacket adapted to surround a waveguide and comprising a first material having a first Young's modulus. A first and a second region may be defined in the cylindrical jacket, extending along at least a portion of a length of the jacket, the first and second regions being disposed opposite each other along a diagonal of the cylindrical jacket and at least one of the first and second regions including a second material having a second Young's modulus higher than the first Young's modulus. The first and second regions may create a preferential bending plane orthogonal to the diagonal.

One or more of the following features may be included. The cylindrical jacket may include or consist essentially of a plastic material selected from polyesters, polyamides, polyether block amides, polyether ketones, polyether sulphones, polyether imides, polyimides, polyethylenes, and/or polyurethanes.

The cylindrical jacket may define an opening having a diameter selected from a range of 0.2 mm to 1.8 mm. At least one of the first and second regions may include a wire. At least one of the first and second regions may include or consist essentially of a material selected from metals, metallic alloys, and plastics. A braid may be disposed within a wall of the cylindrical jacket. The first and second regions may include first and second wires disposed along the braid.

The waveguide may be disposed within the jacket. The waveguide may include at least one defect extending along at least a portion of a length of the waveguide. The defect may be aligned with one of the first and second regions.

In yet another aspect, embodiments of the invention include a waveguide tip for attachment to a waveguide. The waveguide tip includes a cylindrical wall defining (i) a proximal conical opening for fitting over an end of a waveguide; (ii) a distal opening aligned with the proximal opening and adapted for permitting egress of radiation from an output end of the waveguide; and (iii) a conical feature defined between the proximal opening and the distal opening, the conical feature defining a transition from the proximal opening to the distal opening.

One or more of the following features may be included. The cylindrical wall may include or consist essentially of a material selected from titanium, stainless steel, silver, and/or silver coated with silver iodide. A waveguide may be disposed between the conical feature and the distal opening. The proximal opening may have a diameter selected from the range of 0.2 mm to 1.8 mm. The distal opening may have a diameter selected from a range of 0.1 mm to 1.0 mm.

In still another aspect, embodiments of the invention include a waveguide tip for attachment to a waveguide, the waveguide tip including a cylindrical wall defining (i) a proximal conical opening for fitting over an end of the waveguide, the proximal opening defining a cone; and (ii) a distal conical opening aligned with the proximal opening and adapted for permitting egress of radiation from an output end of the waveguide.

One or more of the following features may be included. The cylindrical wall may further define a cylindrical portion between the proximal and distal conical openings. The cylindrical wall may include or consist of a material selected from the group consisting of titanium, stainless steel, silver, and silver coated with silver iodide.

In another aspect, embodiments of the invention include a method for manufacturing a surgical waveguide assembly, including providing a waveguide; and attaching a waveguide tip to the waveguide, the waveguide tip including a conical feature.

In another aspect, embodiments of the invention include a method for manufacturing a surgical waveguide assembly, including providing a waveguide jacket; and attaching a waveguide tip to the waveguide jacket, the waveguide tip including a conical feature.

In yet another aspect, embodiments of the invention include a method for manufacturing a surgical waveguide assembly, including providing a flexible conduit; and attaching a waveguide tip to the flexible conduit, the waveguide tip including a conical feature.

BRIEF DESCRIPTION OF DRAWINGS

FIGS. 2A-2C are perspective and cross-sectional views illustrating a distal tip, with FIGS. 2Aa-2Af being perspective, top, cross-sectional, rear, side and front views, respectively, of the distal tip with handle shown in FIG. 1A, with FIGS. 2Ba and 2Bc showing schematic side views of angled grasping inside the handle and with FIG. 2Bb showing outside grasping of the handle, and with FIGS. 2Ca-2Cc showing a pocket, loops, and wings, respectively, as different shapes of the handle in accordance with embodiments of the invention;

FIG. 3 includes perspective and cross-sectional views illustrating distal tips having various edges and configurations, with FIGS. 3A and 3B being cross-sectional views of FIGS. 3A1 and FIG. 3B1, respectively, with the distal tip of FIG. 3A1 having a cantilevered distal end portion that is blunt on both sides and its tip, while the distal end portion shown in FIG. 3B1 having a sharp tip and blunt sides, and with different configurations shown in FIGS. 3A2-3A4 and 3B2, in accordance with embodiments of the invention;

FIGS. 10A and 10B include perspective and cross-sectional views illustrating a distal tip, with FIGS. 10Aa-10Ac being perspective, top and left-side cross-sectional views, respectively, and FIG. 10B showing the distal tip of FIG. 10Ac with a waveguide positioned within the distal tip, in accordance with alternative embodiments of the invention;

FIG. 18 are schematic views of distal tips without specific tissue interaction region, with FIGS. 18A and 18B being cross-sectional views of FIGS. 18A1 and FIG. 18B1, respectively, with the distal tip of FIG. 18A1 having a sharp spatula distal end portion that is sharp on both sides and its tip, while the distal tip shown in FIG. 18B1 has no spatula, and with different configurations shown in FIGS. 18A2-18A5, in accordance with embodiments of the invention;

DETAILED DESCRIPTION

Figure 1A:
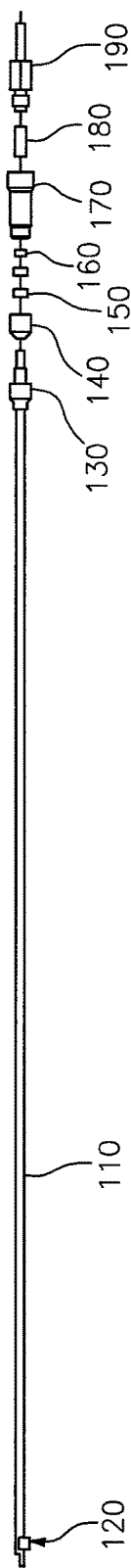
FIGS. 1A-1F are perspective and cross-sectional views illustrating a rotary coupler, with FIG. 1A being a side expanded view of a laser radiation delivery system, FIGS. 1Ba and 1Bb being perspective and expanded views of the rotary coupler shown in FIG. 1A, FIGS. 1Ca-1Cd being perspective, rear, side and front views, respectively, of the rotational end cap shown in FIG. 1A, FIG. 1D being a side cross-sectional view of another rotational end cap shown in FIG. 1A, FIGS. 1Ea-c being side, front and side-cross-sectional views, respectively, of the bearing housing shown in FIG. 1A, and FIGS. 1Fa and 1Fb being side and rear views of the spindle lock nut shown in FIG. 1A, in accordance with an embodiment of the invention.
Figure 1B:
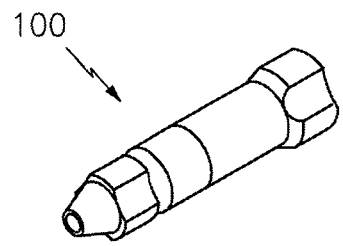
Figure 1B:
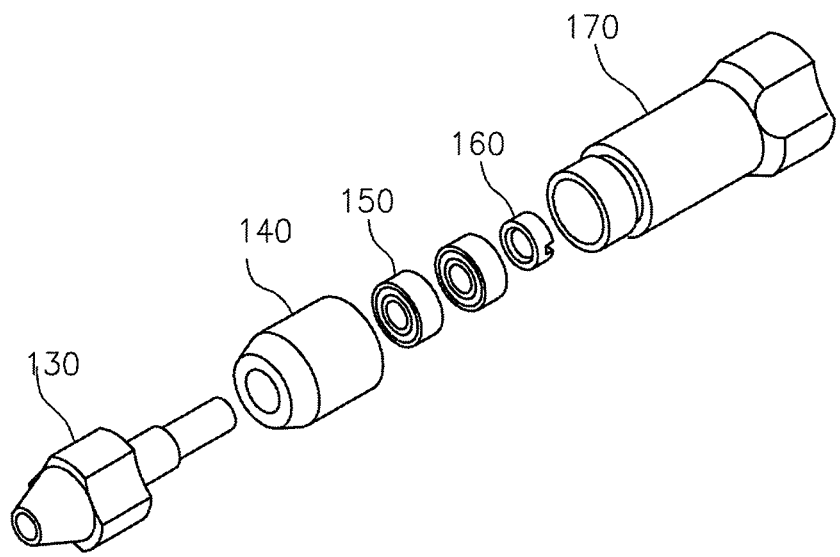
Figure 1C:
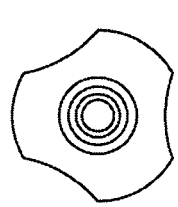
Figure 1C:
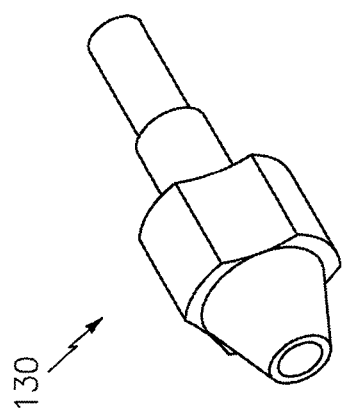
Figure 1C:
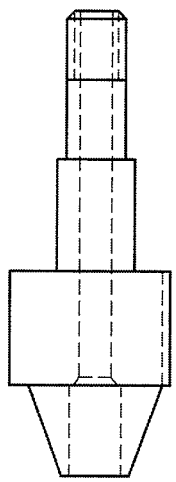
Figure 1C:
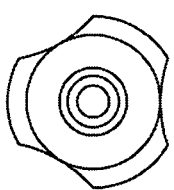
Figure 1D:
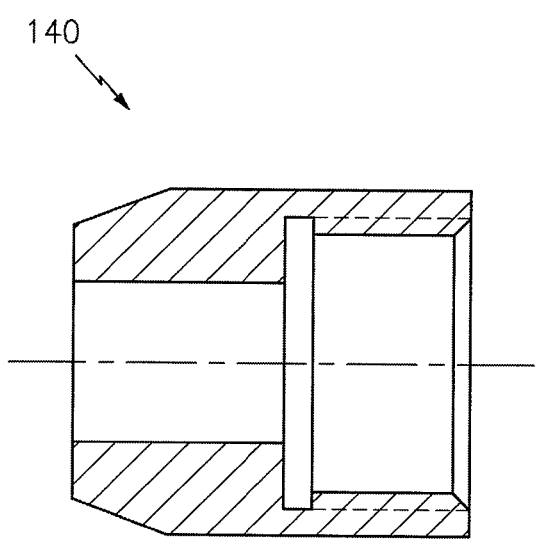
Figure 1E:
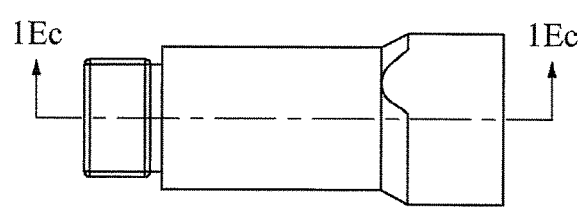
Figure 1E:
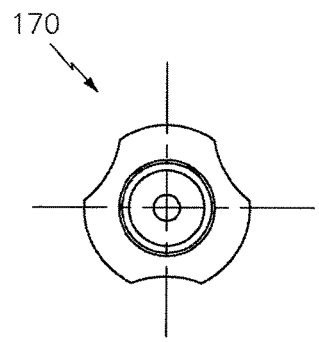
Figure 1E:
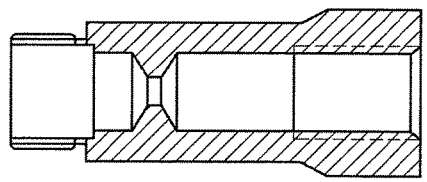
Figure 1F:
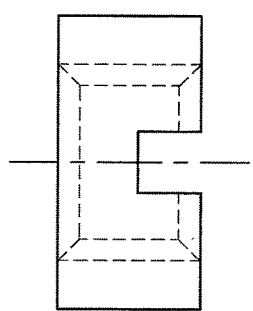
Figure 1F:
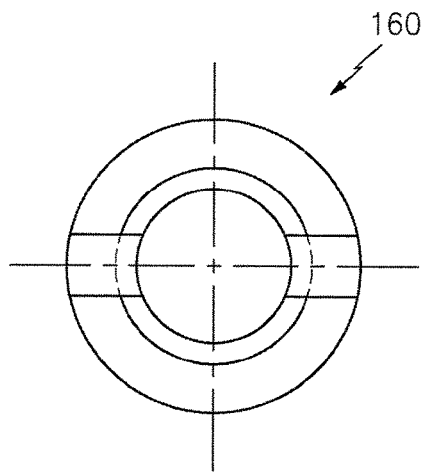

As used herein, "conduit" means a mechanical structure into which a waveguide or waveguide assembly may be placed after the waveguide or waveguide assembly has been manufactured or assembled. A conduit is typically an elongated hollow structure configured to receive a waveguide or waveguide assembly, and may have any cross-sectional profile, e.g., circular, elliptical, square, etc.

As used herein, "tissue debris" means pieces of tissue, fluids, such as blood, and smoke, which can contain particulate matter.

As used herein, "dissection" and "blunt dissection" mean parting or separating the tissue.

As used herein, the portions of the described system elements that are closer to the patient are called "distal," and those closer to the laser are called "proximal."

As used herein, "distal tip" means a unit that may be coupled to a distal end of a waveguide, including at least an inlet for receiving the waveguide and an outlet adapted for (1) permitting egress of radiation from an output end of the waveguide and (2) abutting an end face of the waveguide, the outlet having a smaller diameter than a diameter of the inlet. A "distal tip" may also include a cantilevered distal end portion and a proximal opening that enables a connection to, e.g., a waveguide conduit.

As used herein, "downstream" means distal and "upstream" means proximal.

As used herein, "fluid" means both liquids and gases.

As used herein, "handle" include loops, pockets, sleeves, and wings.

As used herein, an "inlet" is the proximal (closer to the laser) portion of an opening adapted to deliver laser radiation.

As used herein, a "jacket" is a flexible structure that may surround the waveguide. A polymer cladding, as described in U.S. Pat. No. 7,272,285 may be considered, in certain circumstances a "jacket." A jacket may be manufactured at the same time as the waveguide, or placed on it after manufacturing.

As used herein, an "outlet" is a distal (closer to the patient) portion of an opening adapted to deliver laser radiation.

As used herein, "waveguide" encompasses a unitary, physically manipulatable structure that guides waves, suitable for delivering radiation from a laser. It includes optical fiber waveguides, hollow metal waveguides, hollow metalized dielectric tube waveguides, dielectric stack waveguides, and photonic crystal fiber waveguides as well as any other unitary, physically manipulatable waveguide structures suitable for delivering radiation from a laser. As used herein, it does not mean only the region that interacts most directly with the electromagnetic radiation, such as the metal in metalized dielectric tubes, or the confinement region, such as region 110 in FIG. 1A of U.S. Pat. No. 7,272,285.

As used herein, a "waveguide assembly" is a combination of a waveguide with at least a tip and/or a jacket.

As used herein "Young's modulus" means "elastic modulus" and the two are used interchangeably.

Examples of lasers used in such systems include, e.g., $CO_2$, pulsed, and continuous wave (CW). Examples of waveguides used in surgical systems include hollow waveguides and solid waveguides. Elements of such systems include i) jackets and flexible conduits that protect the waveguide and can have other features, such as handles that facilitate grasping and manipulation by handheld surgical instruments, or by robotically manipulated surgical instruments; ii) couplers, such as a device that couples the waveguide to the laser (see U.S. Pat. No. 7,349,589), or that couples the distal tip to the waveguide, or one waveguide to another; iii) handpieces, such as laparoscopes and endoscopes; iv) trocars; v) rigid introducers for flexible waveguides vi) robotic arms, including robotic arms with computer interfaces capable of guiding the surgical tool; vii) manually driven manipulators; and viii) waveguide tips and/or distal tips that themselves may be waveguides, or not, and can serve diverse functions, including resection, dissection, beam shaping, sizing, and positioning, and other functions described in further detail herein. Such system elements can be separable and readily detachable, or integrated and not readily detachable. For example, a tip design may be part of the overall conduit design, or a jacket may be secured via adhesive to a waveguide.

Rotary Coupler

Referring to FIG. 1A, a laser radiation delivery system may include a rotary coupler 100, a flexible conduit 110 attached at a first end to the rotary coupler, and a tip 120 disposed on a second end of the flexible conduit. The laser radiation delivery system may be configured to contain a waveguide assembly, i.e., an optical waveguide disposed in a jacket. The optical waveguide and/or the jacket may have a preferential bend plane. The rotary coupler may serve the purpose of accommodating rotational movement of the waveguide assembly, and permits preferential bending of the waveguide, regardless of the initial orientation and subsequent manipulation of the tip, e.g., by a robotic end effector.

Referring also to FIGS. 1B-1F, the rotary coupler may have a conduit portion and a waveguide portion. The conduit portion may be a rotational end cap 130 including a threaded spindle, adapted for permanently connecting the rotary coupler to the flexible conduit by, e.g., brazing or welding. The waveguide portion is adapted for securing a waveguide assembly, and may include rotational end cap 140, ball bearings 150, a spindle lock nut 160 with a rotational end cap, and a bearing housing 170 with a rotational end cap. The rotational end cap 140 holds the bearings 150. The ball bearings 150 provide low resistance rotation of the waveguide. The spindle lock nut 160 locks the bearings 150 in place. The bearing housing/rotational end cap 170 holds the bearings in place and is adapted to allow the rotary coupler to be connected to a waveguide assembly with a locking nut. An annular gripper 180, made from a compliant material such as silicone, may be preferably disposed within the bearing housing/rotational end cap 170. Compression of the gripper by the end cap 170 and a locking nut end cap 190 restrains the waveguide in the waveguide portion in both longitudinal and circumferential orientations. The waveguide may also be locked by other mechanisms, such as, for example, a push button system or a simple chuck.

The various components of the rotary coupler may be made from any material that is machinable and does not cause an adverse reaction upon contact with human tissue at a relatively short duration, and that is mechanically stable, e.g., metals, ceramics or polymer, including stainless steel, aluminum, titanium, tungsten, gold palladium, plastic, etc. The components of the rotary coupler are also preferably stable with respect to preferred sterilization methods. Metal components may be obtained from, e.g., J & J Machine Company, LLC, based in Marlborough, Mass. Suitable bearings 150 may be, e.g., part number SERI-418ZZMCRA7P25LD, from Alpine Bearing Co. based in Boston, Mass. Suitable tubing for the flexible conduit 110 may be, for example, square lock stainless steel tubing, with an inner diameter of 1.8 mm, and a bend limit of 40 mm, available from Hagitech, based in Dainichi, Japan.

In use, a waveguide assembly is threaded through the locking nut 190 and the rest of the rotary coupler 100, the flexible conduit 110 to which the rotational end cap 130 is welded, brazed, or soldered, and a tip 120 attached to an end of the flexible conduit. The locking nut is tightened to secure the waveguide assembly in the bearing housing/rotational end cap 170. The pressure from the tightening of the locking nut results in the annular gripper 180 that is disposed in the rotational end cap 170 to compressively lock the waveguide assembly in the rotational end cap 170. The flexible conduit and the tip are free to rotate with respect to the waveguide portion and the locking nut.

The rotary coupler allows the rotation of the waveguide assembly disposed in the rotary coupler, flexible conduit, and tip. In particular, the rotary coupler permits relative rotation between the conduit portion and the waveguide portion without any axial shifting of the waveguide assembly relative to the distal tip. This freedom of rotation allows the waveguide assembly to adopt a preferential bend as it is moved during use.

Combination of Distal Tip and Locking Mechanism

As discussed below, a distal tip 120 disposed at a distal end of a conduit may be used to facilitate loading and positioning of a waveguide into the conduit, as the distal tip may be engineered to provide a visibility window which indicates to the user of the position of the waveguide and confirms is properly positioned. The distal tip may also create and define a stand-off distance between the distal end of waveguide and the tissue, and may help reduce the rate of tissue debris build-up on the waveguide during use Furthermore, creating a controlled stand-off distance between the waveguide and the tissue may provide more predictable (controlled) laser-tissue interaction. The distance between the waveguide and the tissue is important because it defines the spot size and power density of the laser beam and thus controls the speed of tissue cutting/ablation as well as allows switching between cutting, ablation, and coagulation modes.

These benefits of the distal tip are preferably realized when the position of the waveguide inside the conduit or handpiece is maintained constant during usage. Maintaining the waveguide position constant is facilitated by locking a proximal portion of the waveguide. Without a proximal locking mechanism, the waveguide may move inside the conduit (handpiece) or even slide out. Accordingly, in an embodiment, a position of a waveguide in a conduit may be determined at a distal end by a distal tip 120 and at a proximal end by a locking mechanism, such as a locking nut end cap 190 or another mechanism, such as, for example, a push button system or a simple chuck or collet.

Distal Tip

Referring to FIG. 2A, distal tip 120 is designed to be attached to a waveguide conduit or waveguide assembly, e.g., a rigid conduit, a flexible conduit, or a waveguide jacket. The tip may be permanently attached to the conduit or waveguide assembly by, e.g., gluing, brazing, welding or soldering, or removably attached thereto, e.g., by a threaded connection or interference fit. The permanent attachment of the distal tip to the conduit or waveguide may increase safety, and provide ease of use and of sterilization. In particular, a safety benefit is provided in the elimination of possibility that an accidentally detached distal tip may be dropped into the patient and perhaps even inadvertently left in the patient. Further, a single integrated device is easier for medical staff to handle than components that need to be assembled. Moreover, an integrated device is more stable, so the possibility of any wobble during use is eliminated. Finally, sterilization is simplified because of the elimination of the possibility of forgetting or losing small parts.

In some embodiments, the distal tip may be permanently attached directly to the waveguide jacket by e.g., gluing, brazing, welding or soldering, or removably attached thereto, e.g., by a threaded connection or interference fit.

In yet other embodiments, the distal tip may be attached directly to a waveguide. Because the assembly is narrower, this configuration may facilitate ease of insertion, make it possible to use trocars having smaller orifices or to access smaller structures for surgeries that do not use trocars, such as otology procedures, and overall facilitate procedures requiring smaller tools and precise beam alignment. In addition, quality control may be simplified, as the assembly may be shipped from a factory with alignment certified, requiring less quality control onsite. Furthermore, the waveguide may be moved closer to tissue, making the spot size smaller, thereby increasing power density and enabling more precise cutting. Finally, by attaching the distal tip directly to a waveguide, the need for a conduit may be eliminated, thereby rendering the system disposable, with no cleaning required.

The distal tip design enhances control of laser/tissue interaction by fixing the distance between an end of the waveguide assembly and the tissue being treated. Moreover, the distal tip enables the performance of general tissue manipulation (moving tissue around) and such operations as blunt dissection. It may also be used to probe (estimate) the depth of the cut performed or dimensions of target tissue, e.g., by use of optional specific marks 225 made on the distal tip. As an example, markings may be spaced 1-2 mm apart to provide a visual reference point for the user. Such markings may provide additional feedback, with the visual indicator supplementing sensory indicators. Moreover, the markings may assist in the evaluation of the size of a feature or spot size of a laser beam, by providing an absolute reference for lateral and/or depth dimensions. An absolute reference may be desirable, in view of the magnified images provided by cameras during surgery.

The distal tip can also facilitate aiming of the laser beam; this may be achieved by configuring the tip such that the laser beam hits tissue next to where the tissue is touched by the tip during use. Facilitating aiming may be particularly useful for wavelengths not visible to the naked eye, such as $CO_2$.

Referring to FIG. 2A, the distal tip has a frame 200 that may be cast or forged from a single piece of material that does not cause an adverse reaction upon contact with human tissue at a relatively short duration, and that is mechanically stable, e.g., a metal, a ceramic, or a polymer, including stainless steel, aluminum, titanium, tungsten, gold palladium, plastic, etc., with detail features machined in the frame. The use of a frame formed from a single piece of material may enhance safety, as the distal tip formed from such a frame is less likely to fall apart from stress applied from multiple directions. Moreover, a single piece design may provide economic advantages, both from a manufacturing perspective (typically less expensive to form a component from a single piece of material rather than from multiple pieces), and an inventory standpoint (fewer parts to track). The entire tip or portions of the tip may be made of transparent material, e.g., glass or polymer (for example polycarbonate), which can be sterilized and is also transparent, thus providing improved visualization. In particular, the transparent material does not block the view or tissue or create a shadow, thereby helping a surgeon see all of the tissue being treated. The cantilevered portion, such as L1 in FIG. 10A, or $d_{265}$ in FIG. 2A may have a visibility enhancement window cut into it (not shown), so that it retains its overall shape and function, but with a transparent hole, or window in it to improve visibility.

Surface properties of the distal tip may be tailored to reduce adhesion of organic matter to the distal tip. This may be achieved by coating the distal tip with a non-stick material (e.g., Teflon™-type polymers or tungsten carbide) or changing the surface finish (e.g., providing a mirror finish, i.e., a smooth highly polished surface produced on metal by mechanical or electrolytic polishing or lapping). An advantage of such surface properties may be the reduction of accumulation of organic matter, e.g., blood or tissue, on the distal tip. This accumulation may impede visualization, may block laser radiation emitted from the distal tip opening, and may lead to a need to replace the waveguide or waveguide assembly during the procedure The frame may define an interface 210 for coupling with a waveguide conduit. For example, the frame may define a proximal opening 220 for attachment to the conduit; the opening may have an inner diameter $d_{220}$ selected from a range of 0.5 mm to 10 mm, for example, about 2.8 mm. In some embodiments, the proximal opening is sized to fit around an outer diameter of the flexible conduit. If the proximal opening is too large, the frame may not stay on the conduit; if the proximal opening is too small, it may not fit onto the conduit. In other embodiments, in which the distal tip is attached to a waveguide jacket, the proximal opening is sized to fit around an outer diameter of waveguide jacket.

The proximal opening 220 may have a configuration based upon the desired mechanical robustness of the junction: the proximal opening may define, for example, a full circle or a half circle. The proximal opening may be a complete cylinder, suitable for a welded junction, or may be designed as a collet, or chuck, with small kerfs cut into it to allow a small amount of expansion so it can fit over a male part.

In an embodiment, the frame defines an inlet 230 downstream of the interface 210. The inlet may serve the function of positioning the waveguide, and may help position the waveguide distal to the proximal opening 220. The inlet may be a second opening sharing a central axis with the proximal opening disposed collinearly upstream therefrom, the second opening being sized for receiving a waveguide, e.g., a waveguide assembly including a waveguide and a jacket. The inlet may have an inner diameter $d_{230}$ selected from a range of 0.2 mm to 5 mm, for example, about 1.7 mm. The inlet is sized to receive the waveguide. If the inlet is too small, the waveguide may not fit into the inlet. If the inlet is too large, the waveguide may not be centered in the inlet, and may be difficult to control.

The diameter of the proximal opening may be larger than a diameter of the inlet, to facilitate attachment of the waveguide conduit while also allowing accurate control of the positioning of the waveguide assembly. The inlet may be disposed 1 mm to 5 mm, preferably about 3 mm from the proximal opening. This distance is selected to be sufficiently small to not adversely affect mechanical robustness and to not limit the flexibility of an excessively long portion of the flexible conduit.

The tip may include an outlet 240 permitting egress of radiation from an output end of the waveguide. This outlet may define a distal stop for the waveguide assembly, disposed collinearly downstream from the inlet, e.g., downstream from the second opening. The distal stop may be an opening having an inner diameter smaller than an outer diameter of the waveguide assembly, e.g., the distal stop may be an opening aligned with the second opening and having an inner diameter $d_{240}$ selected from a range of 0.05 mm to 4.99 mm, for example, about 1.2 mm. The size of the distal stop opening may be selected to not block outgoing laser radiation and, at the same time, to protect a distal end face of the waveguide assembly from tissue debris accumulation and/or splatter, splashing and deposition during use. The distal stop serves to block the movement of the waveguide assembly in the conduit beyond the tip.

A handle 250 may be defined below the proximal opening. This handle may be sized and adapted for mating with a manipulator, for example, for grasping by an end effector, e.g., pincers, clamps, or jaws (ribbed or flat) of the manipulation tool. The manipulator may be attached to, and controlled by a robot. Such control may be achieved by a human operator, or by a set of predetermined computer instructions, or by a combination of a human operator in real time and a set of predetermined computer instructions. For example, the human may translate the surgical tool in a direction essentially parallel to the tissue, while the robot, with position sensing input, adjusts the position of the waveguide in a direction perpendicular to the tissue, so as to maintain a constant spot size and power density. A suitable manipulator with ribbed jaws is, for example, the EndoWrist® Needle Driver, available from Intuitive Surgical, Inc.

Figure 2B:
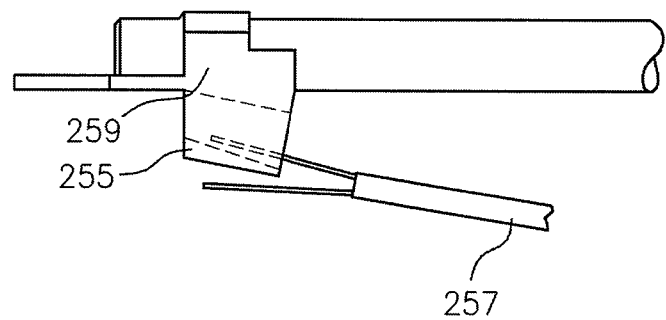
Figure 2B:
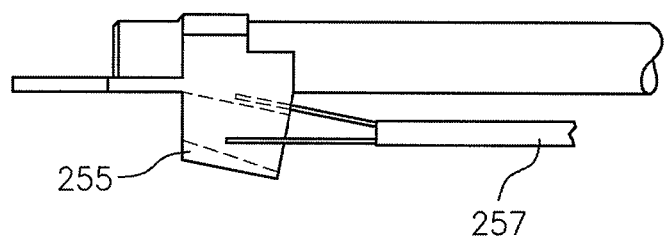
Figure 2B:
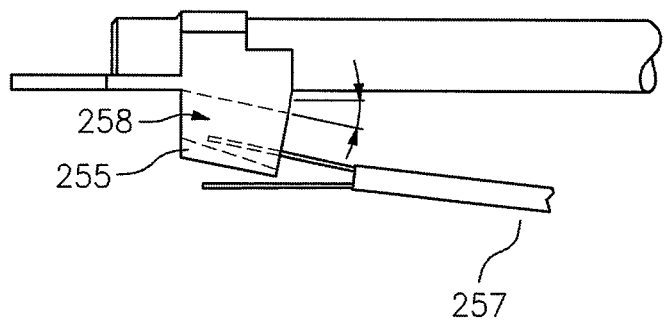

The handle may be defined by an opening in the frame disposed below the interface. The handle may be in the form of a flat handle with grooves or ribs to improve holding stability, as shown in FIG. 2A. In a preferred embodiment the handle is in the form of a handle frame 255 suitable for grasping by insertion of one of the manipulator jaw or pincer into the handle frame opening and clamping the handle frame with the other jaw or pincer of the manipulator, as shown in FIG. 2A. Referring to FIGS. 2A and 2B, the handle frame is preferably rectangular and allows grasping on any of three sides. This capability provides an ergonomic advantage by allowing doctors to grip the handle frame from different directions. Moreover, flexibility in gripping angle helps with the visualization of target tissue, as the manipulator 257 may be kept out of the line of sight to the end of the distal tip. The handle frame may be sized to match the size of the manipulator, for example the handle opening may be 1 mm×1 mm, or 2 mm×2 mm, or 3 mm×3 mm, with the handle frame thickness being at least 0.1 mm, e.g., 0.2 mm, or 0.3 mm, or 0.4 mm or thicker. Different sides of the handle frame may have different thicknesses. The handle opening may define an angled entry 258 for the manipulator 257. Advantages provided by the angled entry may include avoidance of mechanical interference between the manipulator and the conduit or waveguide, as well as improved visualization. In some embodiments, the handle opening may define a straight entry 259.

Figure 2C:
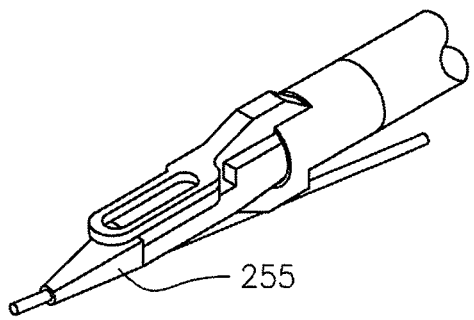
Figure 2C:
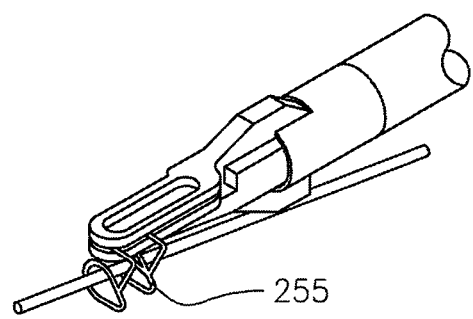
Figure 2C:
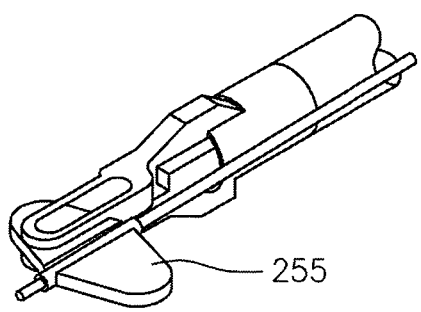
Figure 4A:
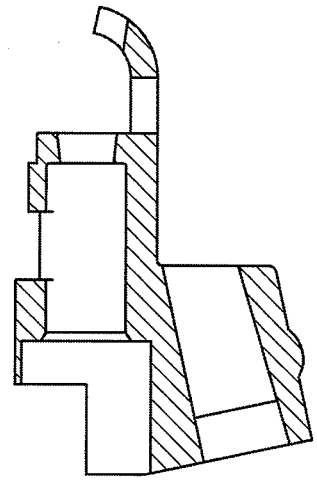
FIGS. 4-6 are perspective and cross-sectional views illustrating a distal tip, with FIGS. 4Aa-4Ae showing side, front, side-cross-sectional, perspective and top views, respectively, of a distal tip having a cantilevered distal end portion with an half annulus and open region, with FIGS. 5Aa-5Ae showing side, front, side-cross-sectional, perspective and top views, respectively, of an alternative distal tip having a bent and grooved cantilevered distal end portion, and with FIGS. 6a-g being top perspective, left side, rear, right-side-partial-cross-sectional, rear and perspective views, respectively, of yet other distal tips with a partial-cross-sectional view of the tip of FIG. 6b shown in FIG. 6g, in accordance with embodiments of the invention.
Figure 4A:
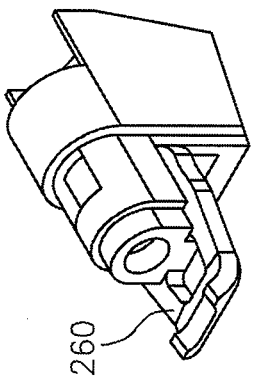
Figure 4A:
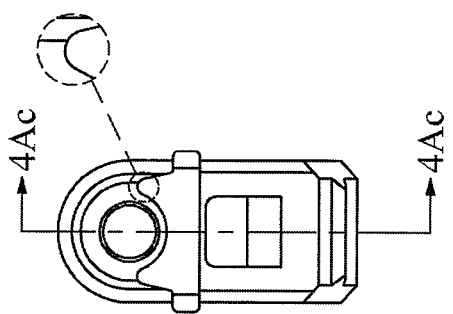
Figure 4A:
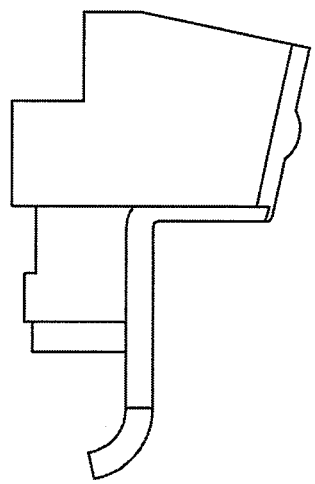
Figure 4A:
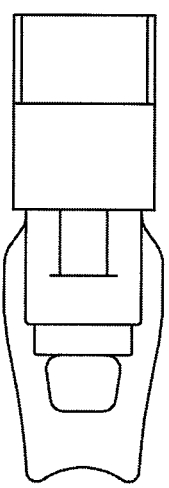
Figure 5A:
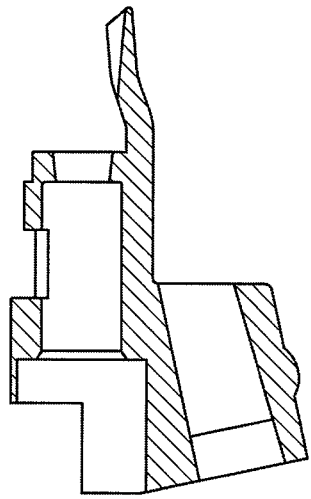
Figure 5A:
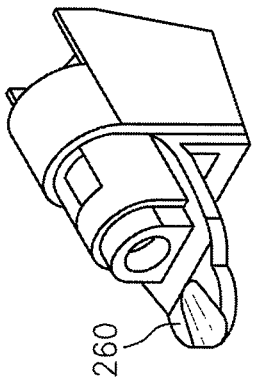
Figure 5A:
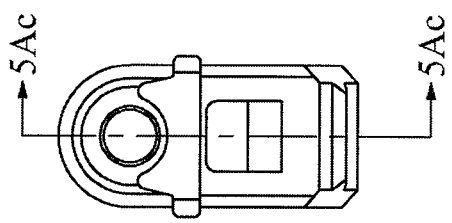
Figure 5A:
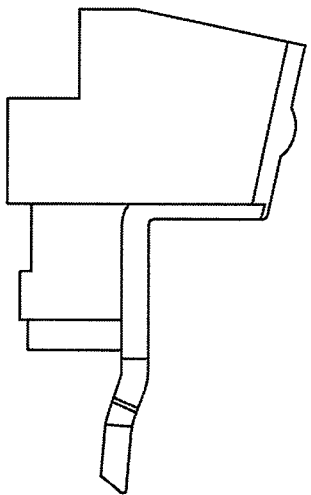
Figure 5A:
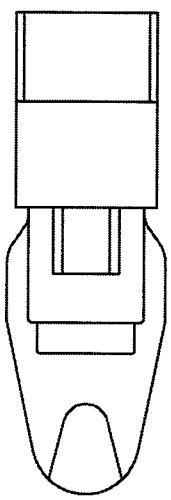
Figure 6B:
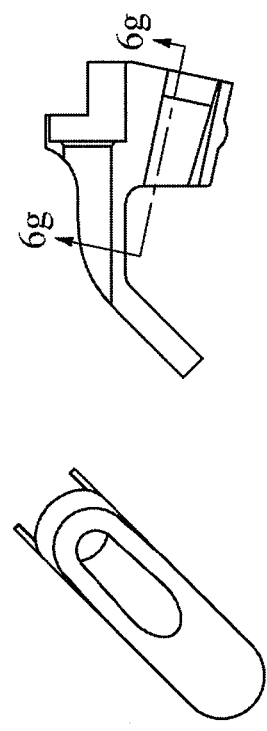
Figure 6A:
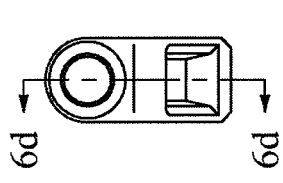
Figure 6D:
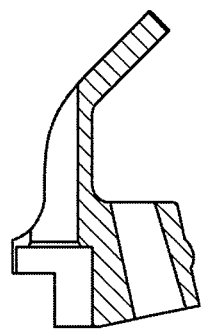
Figure 6C:
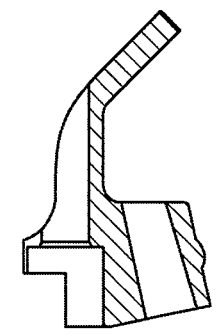
Figure 6F:
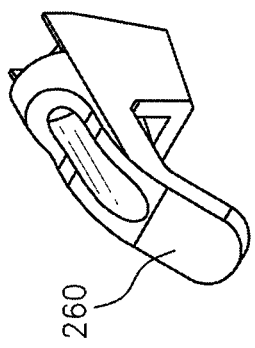
Figure 6G:
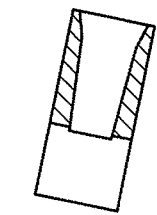
Figure 6E:
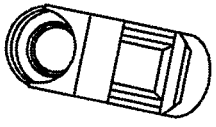

Other concepts for the shape of the handle 255 may be loops, pockets, sleeves, or wings as shown in FIG. 2C. A further concept is to shape the tip so that it is adapted for mating with a particular grasper, such as a hexagonal cross section with an open hexagonal socket. Such a design may offer opportunities for calibrated and controlled rotation to access different edges or portions in a tip having a blunt and sharp edge. The primary requirements for the handle are a geometric and functional match to the gripping device, and sufficient mechanical robustness. A geometry which permits easy visualization of the surgical site is also desirable.

The frame may also define a cantilevered distal end portion 260 that may extend beyond the distal stop. The cantilevered distal end portion is adapted for tissue manipulation, such as blunt dissection and cutting. The cantilevered distal end portion may have a visibility enhancement window cut into it so that it retains its overall shape and function, but with a transparent hole, or window in it to improve visibility.

A thickness and aspect ratio of the cantilevered distal end portion 260 may be selected to make it suitable for tissue manipulation. Accordingly, it preferably extends beyond the distal stop, and its aspect ratio is such that it is wider than it is thick. A preferred aspect ratio of width to length is >1:1, e.g., 6:1. If the end portion 260 is too wide, it will block the view of the tissue during a procedure, making manipulation more difficult. Preferably, the end portion 260 has a width selected a range of 1-10 mm, e.g., 3.6 mm.

If the end portion 260 is too thin, it may bend or break. If it is too thick, it may be capable of only pressing on tissue, rather than dissecting it. Preferably, a thickness of a center region of the end portion 260 is selected from a range of about 0.4 mm to about 3 mm. Furthermore, the end portion 260 provides control of the distance between a tip of the waveguide assembly and the tissue, an important aspect for consistent laser/tissue interaction. A maximum length of the end portion is determined by beam expansion. Preferably, the end portion is sufficiently short such that, in use, the laser beam does not hit the cantilevered distal end portion, thereby heating it. A minimum practical length of the cantilevered distal end portion 260 is 1 mm.

Referring to FIG. 3, the end portion 260 may have a sharp edge 300 suitable for cutting tissue. For example, a thickness of the sharp edge may be less than 0.4 mm. In some embodiments, the end portion may have a blunt edge suitable for dissecting tissue, i.e., for blunt dissection or probing and tissue manipulation, e.g., the blunt edge 310 may have a thickness greater than 0.4 mm. In some embodiments, the cantilevered distal end portion 260a-260f may be a half cylinder shape, one portion of which remains blunt, while one or more edges has been sharpened and adapted for tissue cutting. Versatility in terms of multiple functionality is provided by combining blunt and sharp edges in a single distal end portion. Accordingly, this configuration allows fewer tools to be used in a single procedure, thereby reducing the number of time-consuming tool exchanges that may need to be performed.

In an embodiment (not shown), the cantilevered distal end portion may have a serrated edge.

In an embodiment, sharp edge 300 may be recessed from a distal end of cantilevered distal end portion, thereby permitting flexibility in the engagement of the sharp edge by the surgeon. Thus, the surgeon may access the sharp edge by changing an angle of the distal tip, without necessarily requiring the use of another tool.

The cantilevered distal end portion 260 may be used to probe a depth of a cut in the tissue, to assess the dimensions of features of the tissue, and to perform general tissue manipulation, e.g., to expose fresh tissue to the laser beam or to apply tension to the tissue during cutting, as well as to cut tissue.

The cantilevered distal end portion 260 may also facilitate aiming of the laser beam exiting the waveguide at the tissue. The cantilevered distal end portion may be designed to provide a visual indicator of the location and divergence of the laser beam on the tissue, as the laser beam is guided by the waveguide assembly whose distal end is placed in the distal tip. For example, it may have a contour, such as a distal jagged edge, or an indicia indication to facilitate the aiming of the laser light transmitted through the waveguide assembly. This feature may be particularly helpful for surgeons. Since laser radiation is invisible, a visual indicator of where a laser beam hits tissue helps surgeons to aim the laser beam at the tissue portion to be cut or dissected. An accurate indicator of the beam's location may provide the safety benefit of reducing the possibility that healthy tissue may be damaged. The visual indicator may be especially useful with waveguides that provide non-centered laser radiation.

Referring to FIG. 2A as well as FIGS. 4, 5, and 6, the cantilevered distal end portion 260 may be flat, bent, grooved/curved, or angled, respectively. The shape of the end portion 260 may assist with tissue manipulation, e.g., with moving tissue. Moreover, the shape of the tip may assist with the visualization of the placement of a beam in, e.g., an organ during a procedure.

Referring to FIG. 4, cantilevered distal end portion 260/ tissue interaction region L1 may also be designed as an annulus, or half annulus, with an open region corresponding to the place where the beam is expected to hit.

Referring to FIG. 2A, a stand-off distance $d_{265}$ is defined by a distance that the cantilevered distal end portion 260 extends beyond the proximal edge of the distal stop, that is the distal most edge of the waveguide. Accordingly, a laser beam guided by the waveguide assembly may be kept a consistent distance from target tissue. The stand-off distance $D_{265}$ may be, selected from a range of 1 mm to 10 mm, for example, 4.3 mm. The selection of the stand-off distance may be based on the particular application, including the organ which is to be treated, and on beam expansion from the waveguide.

Figure 7A:
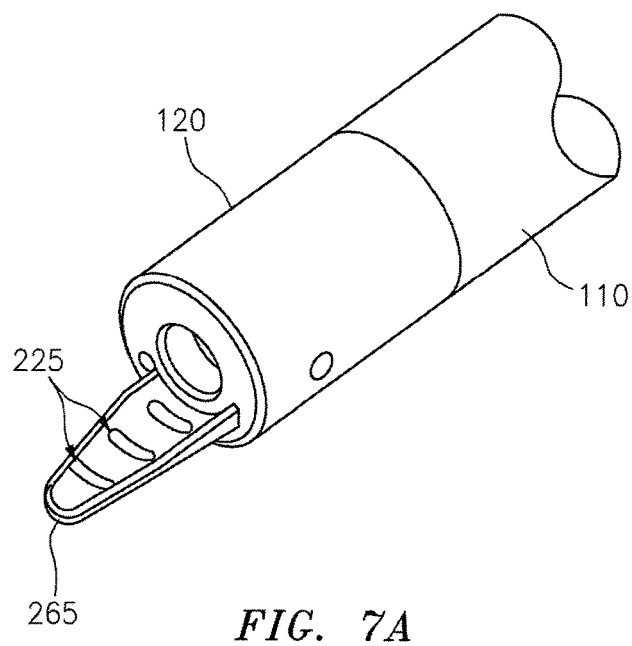
FIGS. 7A and 7B are perspective and side-cross-sectional views of a distal tip having a cantilevered distal end portion extension, in accordance with an embodiment of the invention.
Figure 7B:
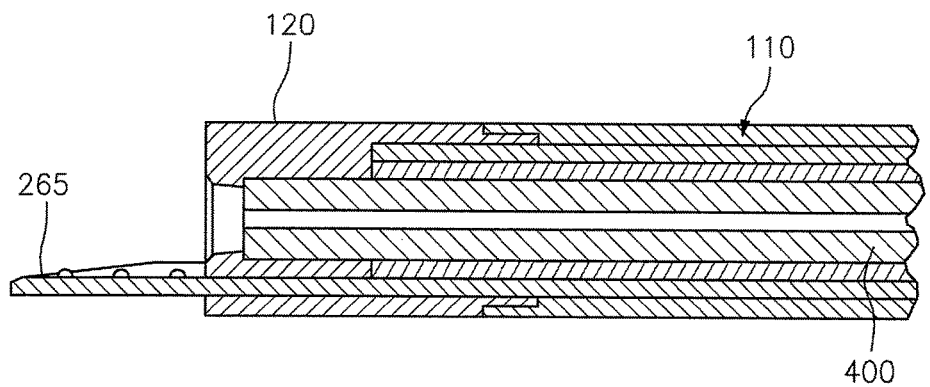

In some embodiments, control of the stand-off distance may be accomplished by adjusting the length of the cantilevered distal end portion. Accordingly, referring to FIGS. 7A and 7B, in some embodiments the cantilevered distal end portion extension 265 may be engineered to have an adjustable length, and controlled by the user. For example, the cantilevered distal end portion may be made as a separate piece that is held by the distal tip holder and is connected to a control wire passed through an additional lumen made in the flexible conduit 110. The control wire may passed in parallel to waveguide 400 to the proximal end of the flexible conduit, where a mechanism for advancing and retracting the control wire may be added. Suitable methods of articulating the distal portion of an instrument by control wires are known to those of skill in the art. Many laparoscopic surgical instruments, such as graspers or shears, are articulated by such mechanisms. An example is Pilling flexible endoscopic forceps catalog number 505686, available from Teleflex Medical, based Research Triangle Park, N.C., in which control wire retraction and extension is used to articulate a forceps tip about its pivot.

Figure 7C:
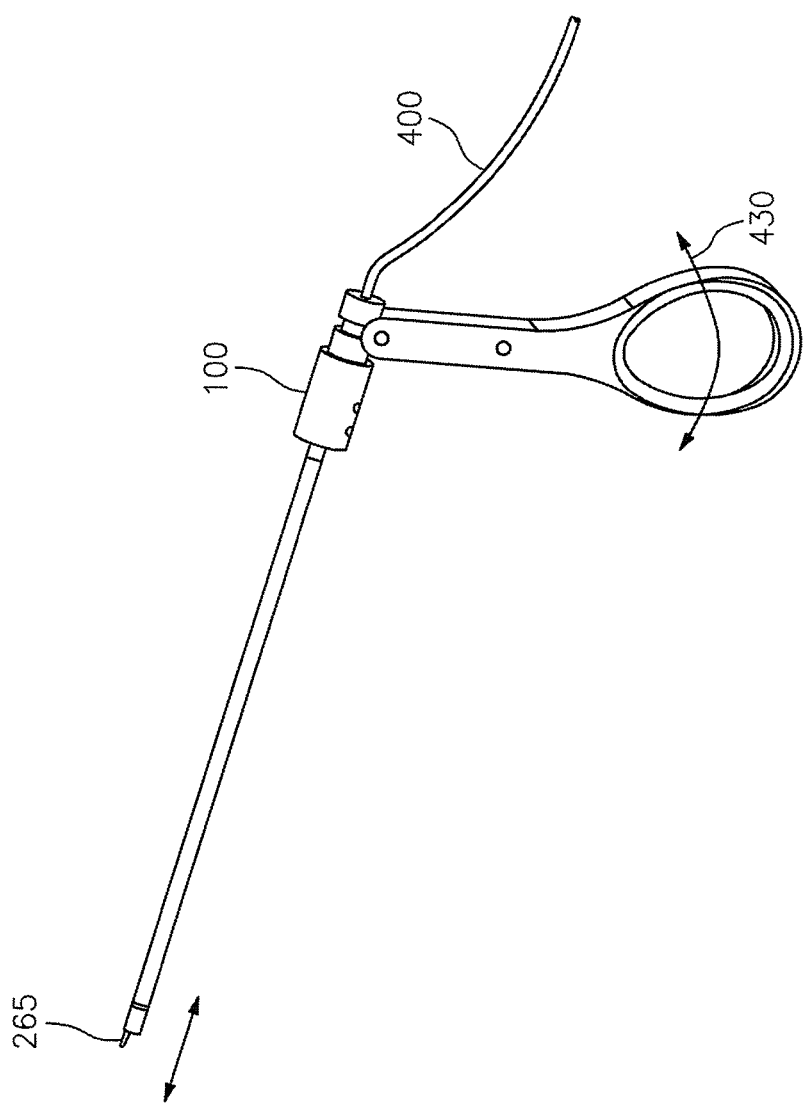
FIG. 7C is a perspective view of a conduit with a cantilevered distal end portion having an adjustable length and with an actuating mechanism, in accordance with an embodiment of the invention.
Figure 8:
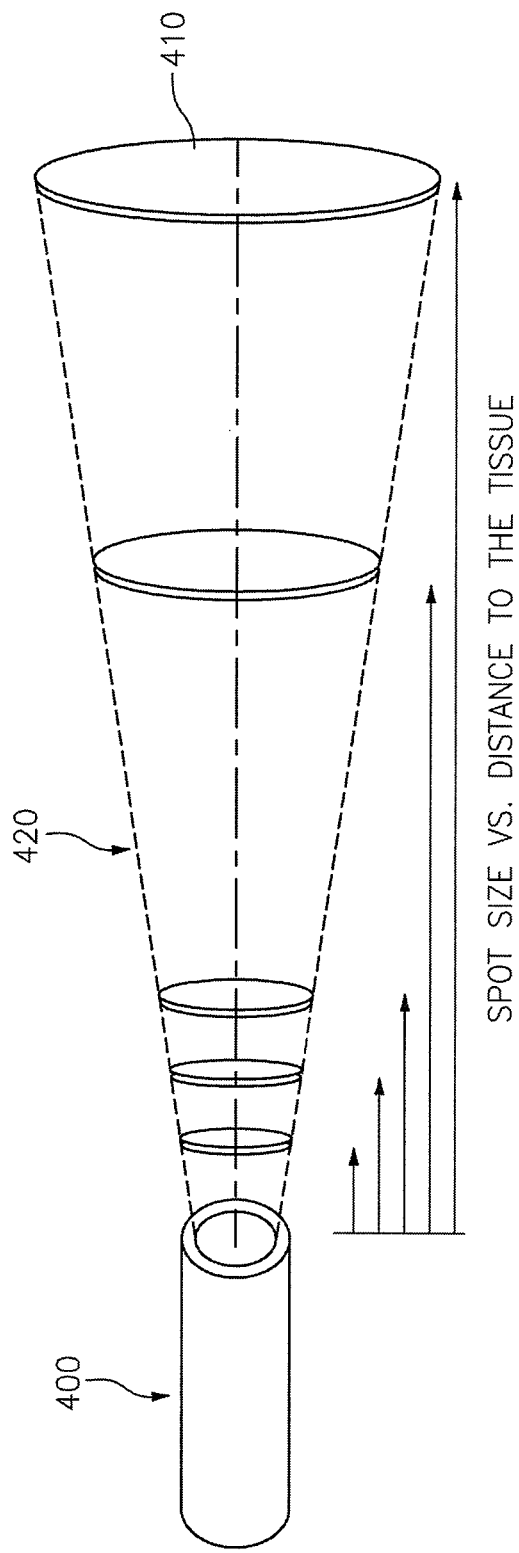
FIG. 8 is a perspective view of a diverging beam, with spot size increasing with distance to target tissue.
Figure 9C:
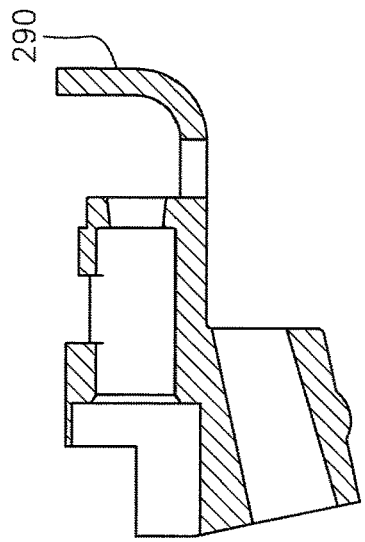
FIG. 9 includes perspective and cross-sectional views illustrating a distal tip, with FIGS. 9a-9e showing left side, front, right-side-cross-sectional, perspective and top views, respectively, of the distal tip having a cantilevered distal end portion with a backstop, in accordance with an embodiment of the invention.
Figure 9D:
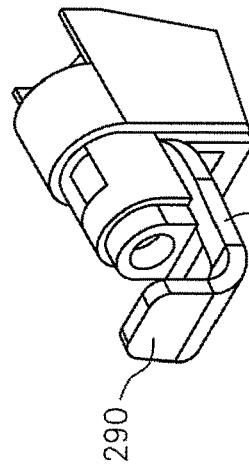
Figure 9B:
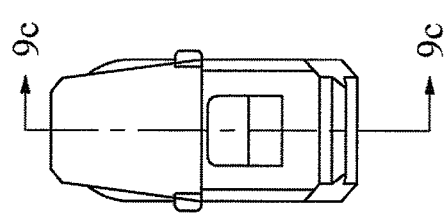
Figure 9A:
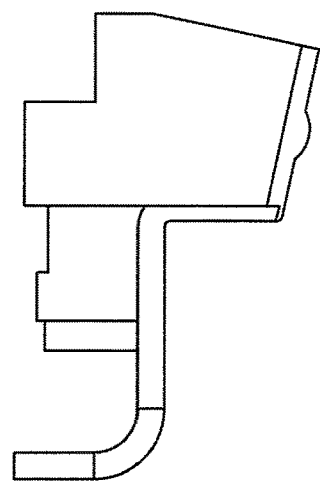
Figure 9E:
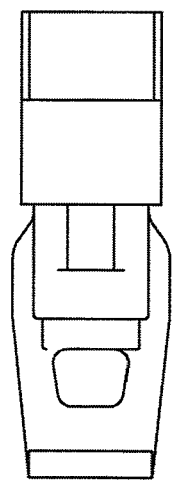

Referring to FIG. 8, a tip with a variable cantilevered distal end portion length may allow one to select a spot size. The illustration of the cone of radiation emerging from the waveguide 400, e.g., fiber shows how selecting the stand-off distance determines the spot size. The spot side may be determined by directing the laser at a wooden tongue depressor, or at a fluorescent sensor plate, such as a Lumitek model CF-16. The spot size 410, for a given waveguide beam divergence 420 may be set during manufacturing, after the product has been sold but before surgery, by the surgical staff, or after or during a procedure. It may be possible to set the stand-off distance once, or many times. The stand-off distance may set be using a push or pull mechanism in the conduit. An example of such an actuator is shown in FIG. 7C, in which a thumb ring linkage 430 is connected to a coupler, e.g., rotary coupler 100 through which the waveguide 400 is positioned, allowing a surgeon to adjust a position of the position of the cantilever The spot size of the laser radiation emitted from the distal tip affects the power density of the laser energy and thereby defines laser tissue interaction, e.g., cutting or ablation mode, and cutting or ablation rate. In general, a beam exiting optical waveguide diverges as shown in FIG. 8. Therefore, spot size may be controlled by setting a distance between an exit point of the laser radiation and the tissue, i.e., by control of the stand-off distance.

Another way to control the distance between waveguide and the tissue may be by using a proximity sensor built into the waveguide, jacket, or conduit. This proximity sensor may measure a distance to the tissue and provide a feedback to the user or computer interface. Distance may be controlled by the user or preprogrammed into a computer that automatically maintains a preset distance by adjusting the position of the manipulator.

Referring again to FIG. 2A, the distal tip may have ribbed sides 280 to facilitate being grasped by a manipulator tool, as discussed above.

One or more through holes 270 may be provided proximate the inlet 230 to enable visualization of the position of the waveguide in the distal tip to ensure correct placement. Correct placement of the through holes may facilitate control by the user of the spot size and thus energy density. Also, correct placement of the waveguide contributes to safety. In particular, the waveguide is preferably positioned to avoid beam clipping by the cantilevered distal end portion, i.e., positioned such that the beam does not hit metal, which may result in the metal being heated up, possibly burning tissue. See FIG. 10B and related text for further discussion about beam clipping. The cantilevered end of the tip can be shaped to block propagation of laser radiation after a certain distance from the exit point from the waveguide. Referring to FIG. 9, the cantilevered distal end portion of the distal tip may be configured to include a backstop 290. The backstop may be inserted under a layer of tissue being treated with a laser, so that the tissue behind the backstop is protected from the laser. The backstop may be made of metal, ceramics or glass. In an embodiment, a distance between exit point of the laser beam from the waveguide and the backstop ($d_{290}$), and a thickness of the backstop are the most critical parameters. Distance $d_{290}$ is dictated by the desired spot size of the laser beam interacting with tissue and by thickness of the tissue. For practical reasons, this distance may be selected from a range of 3 mm to 20 mm. A thickness of the backstop may be defined based on the thermal properties of the backstop material and maximum laser energy that can be potentially absorbed by the backstop without exceeding certain threshold temperature. For example, target threshold temperature may be set at 60° C. to avoid denaturing of the proteins contains in the tissue. For practical reasons, a thickness of the backstop may be selected from a range of 0.5 mm-10 mm.

Figure 10B:
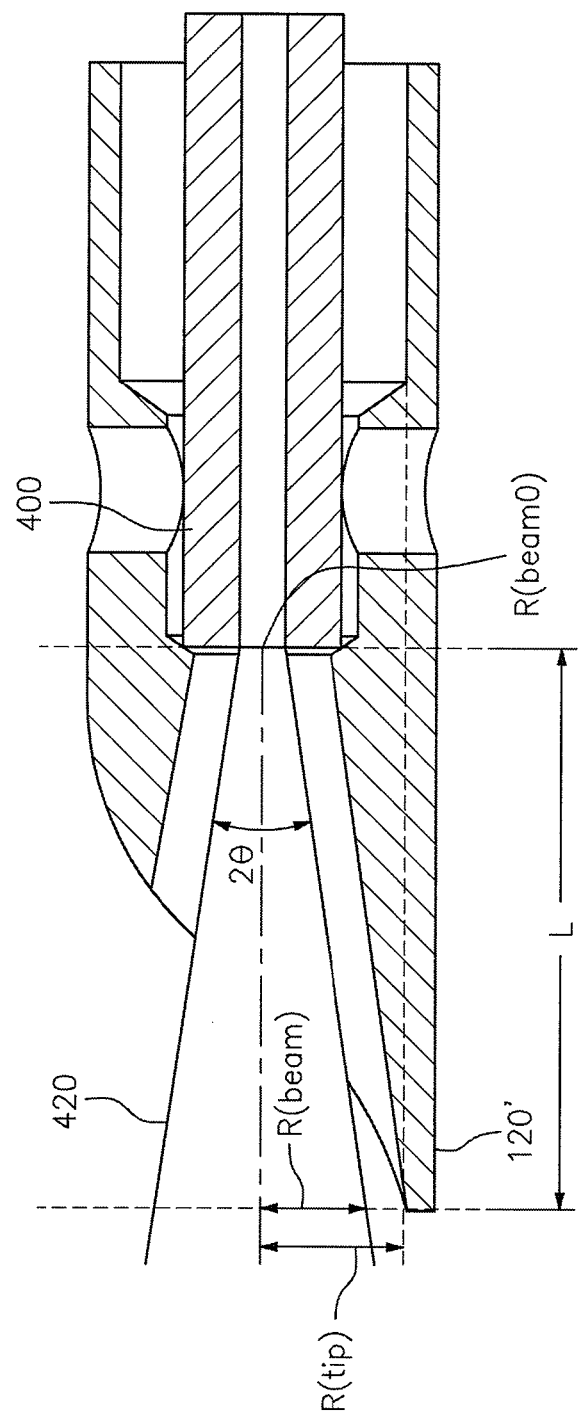

Referring to FIGS. 10A and 10B, a distal tip 120' in accordance with an embodiment of the invention may be suitable for coupling with a rigid conduit and, accordingly, may not have a handle 250, as the distal tips of this embodiment are not intended to be grasped by a manipulator such as an end effector. The distal tip may include a cantilevered distal end portion 260, i.e., a tissue interaction region L1. A protection region 405 (region L2) of the cantilevered distal end portion proximate the outlet 240 may serve to protect the waveguide. A positioning region 410

(region L3) may include the interface 210, and may help position the waveguide. Coupling region 420 (region L4), including proximal opening 220 may be used to attach the distal tip to the conduit. Exemplary dimensions and functions of the different regions are indicated in Table 1. Opening 270 in the distal tip may be used to visualize the position of the waveguide, as well as to visualize the position of the waveguide jacket during assembly and for applying adhesive.

Figure 11A:
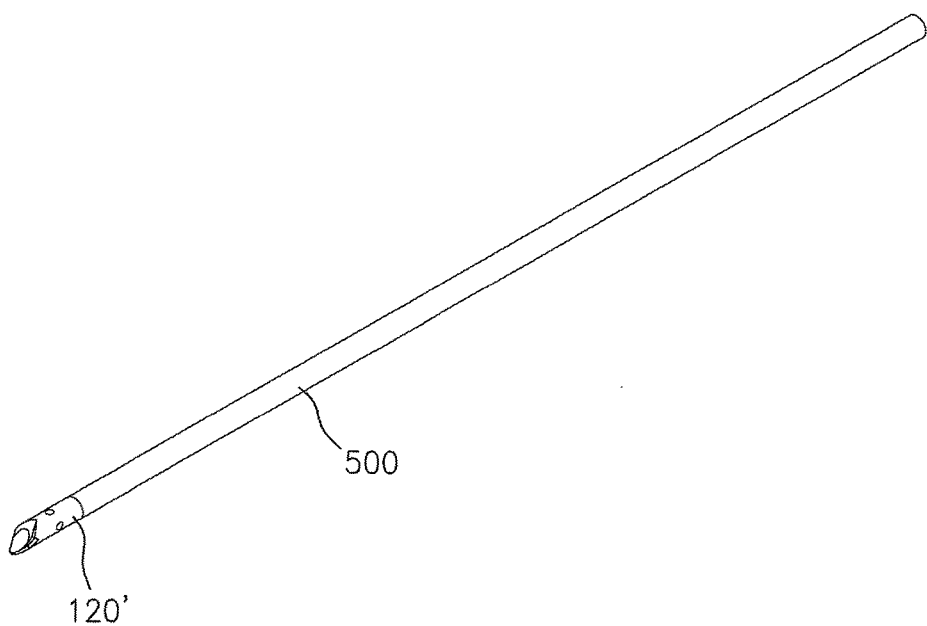
FIGS. 11A-11B are schematic views illustrating a distal tip configured to be attached to a rigid conduit and coupled thereto, in accordance with embodiments of the invention.
Figure 11B:
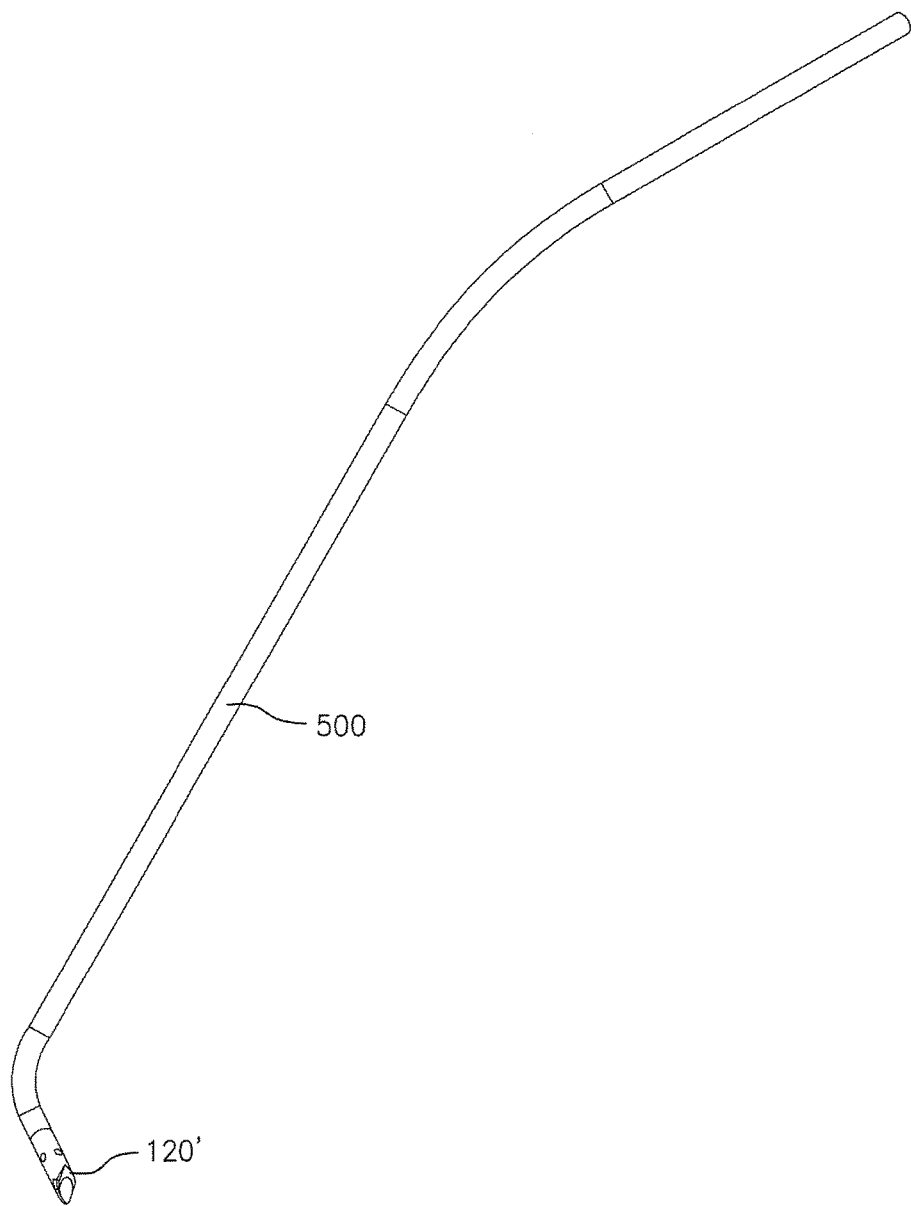
Figure 12A:
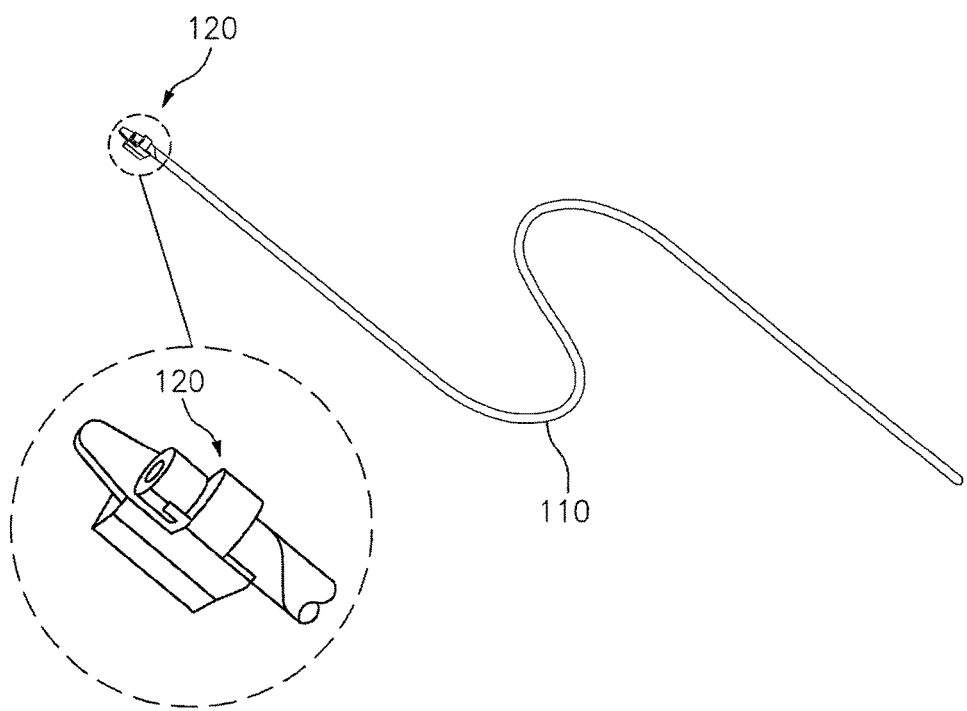
FIGS. 12A-12B are schematic views illustrating a distal tip configured to be attached to a flexible conduit and coupled thereto, with FIG. 12Bb being an enlarged view of the distal tip in FIG. 12Ba, in accordance with embodiments of the invention.
Figure 12B:
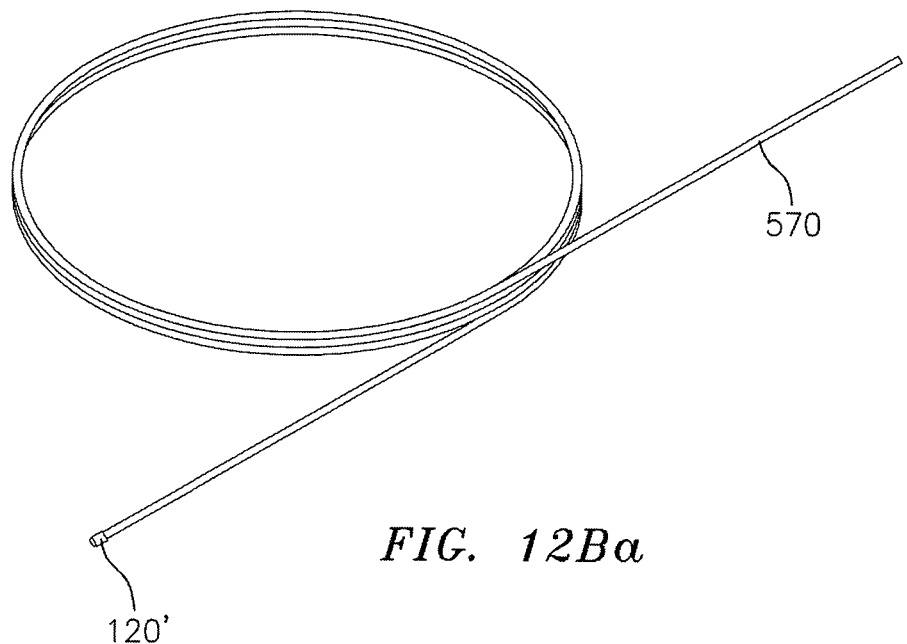
Figure 12B:
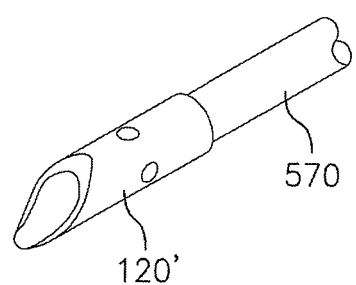

In various embodiments, the distal tip 120' may be configured to be attached to a rigid conduit 500, i.e., have an interface sized and shaped to couple to a rigid conduit (see FIGS. 11A-11B), The distal tip 120' may also be configured to be attached to a flexible conduit 110, i.e., have an interface sized and shaped to couple to a flexible conduit (see FIG. 12A) or directly to a waveguide in a jacket 570, i.e., have an interface sized and shaped to couple to a waveguide in a jacket (see FIG. 12B). When the distal tip is placed directly on a waveguide in a jacket, the distal tip may not have a distinct proximal opening 220; rather the positioning region 410 (region L3) may serve both to position the waveguide and to connect thereto. In alternative embodiments, the distal tip 120 including a handle may be configured to be attached to the rigid conduit 500, flexible conduit 110, or waveguide in a jacket 570.

The aperture of the outlet is defined by R (tip). For design purposes, dimensions of the distal tip are preferably chosen so that R(tip) is greater than R(beam), as shown in FIG. 10B. R(beam) is defined by the equation $$R(\text{beam}) = R(\text{beam0}) + L \times \tan \theta,$$

where $\Theta$=divergence of the diverging beam 420 exiting from the waveguide 400 (half angle), and R(beam0) is a radius of the laser beam at the exit from the waveguide. For example, typical values for an OmniGuide hollow waveguide used at 10.5 μm wavelength are:

R(beam)=10-1000 μm $\theta$=2-15°

Thus, for a particular laser beam divergence, it can be seen that R(tip) will increase for longer tips, to help avoid obstructing the output of a diverging laser beam.

Figure 13:
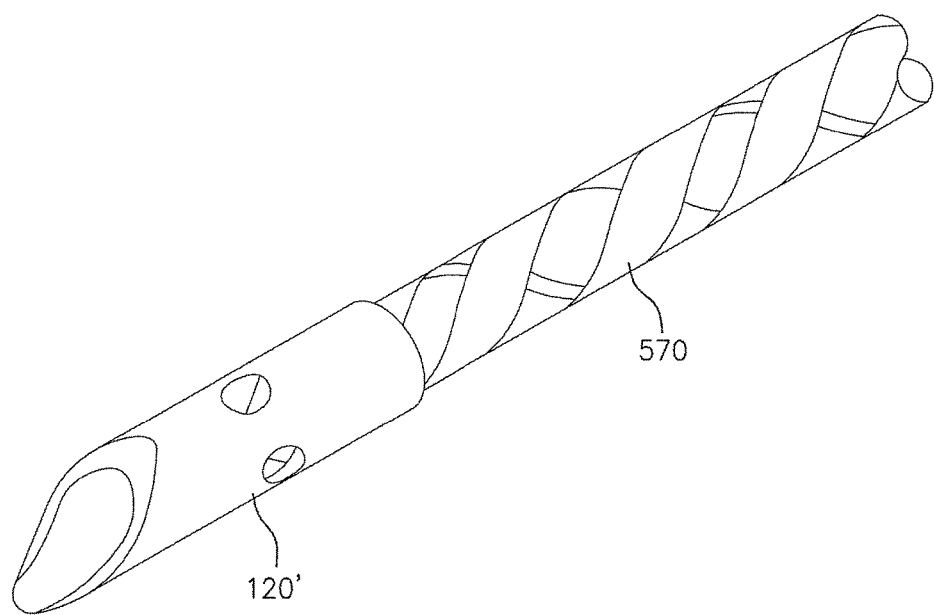
FIG. 13 is a schematic view of a female distal tip disposed on a waveguide assembly, in accordance with an embodiment of the invention.
Figure 14:
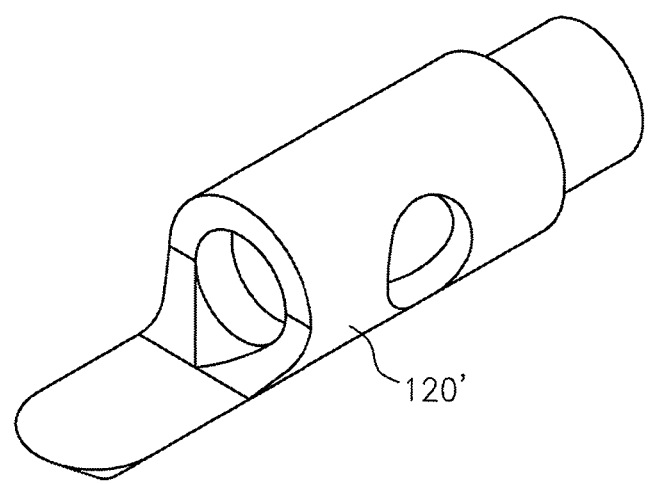
FIG. 14 is a schematic view of a male distal tip in accordance with an embodiment of the invention.

Depending on the part to which the distal tip is attached (i.e., rigid conduit, flexible conduit, or waveguide assembly), the distal tip 120' may be male or female. See FIGS. 13 and 14, for an example of a female distal tip 120' on a waveguide assembly including a jacket 570 and, and for an examples of a male distal tip 120', respectively.

Figure 15:
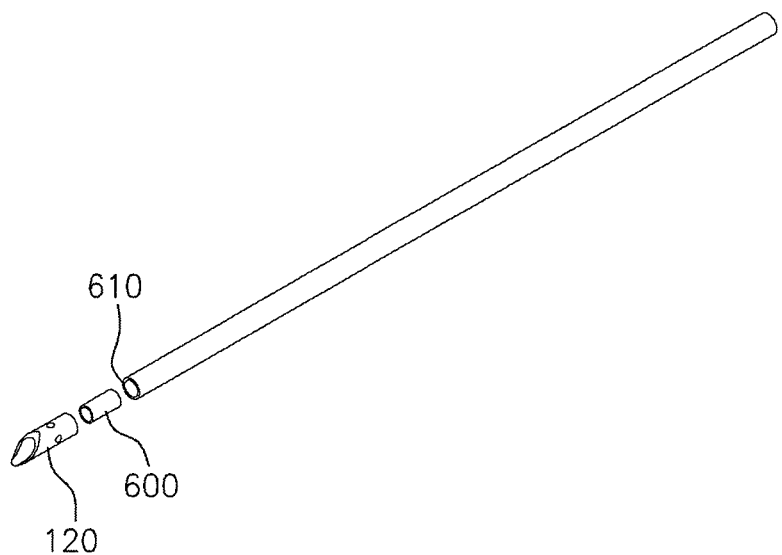
FIG. 15 is a schematic view of a coupler disposed between a distal tip and a cannula portion of a conduit in accordance with an embodiment of the invention.

Referring to FIG. 15, a coupler 600 may be disposed between a distal tip 120 and a cannula portion 610 of the conduit. The coupler may have either male or female termini.

TABLE 1

| Tissue interaction | Positioning of waveguide | | Connection to conduit |
|---|---|---|---|
| L1 | L2 | L3 | L4 |
| Blunt dissection | Waveguide protection | Centering | Threading |
| Resection | Shielding | Hard stop | Press fit |
| Cutting | | Connection to waveguide | Brazing |
| | | Visualization of the position of the waveguide | |
| Aiming | Waveguide centering | | Laser weld |
| Haptic feedback | Axial alignment | | Adhesive |
| Biopsy/tissue removal | | | Rivet |
| Tissue manipulation | | | Rotary/push connector |
| Measuring | | | Luer lock |
| Fluid escape | | | Connection to OD or ID |
| Laser radiation backstop | | | Permanent or non-permanent |
| Distal control | | | |
| Beam expansion | | | |
| ID1 | ID2 | ID3 | OD |
| 10 μm-3 mm | 100 μm-5 mm | 125 μm-6 mm | 125 μm-8 mm |
| L1 (mm) | L2 (mm) | L3 (mm) | L4 (mm) |
| 0-1 | 0-1 | 0-1 | 1-10 |
| 0-2 | 0-2 | 0-2 | 1-20 |
| 0-3 | 0-3 | 0-3 | 1-50 |
| — | — | — | 1-100 |
| — | — | — | 1-200 |
| 0-10 | 0-10 | 0-10 | 1-600 |

Figure 16:
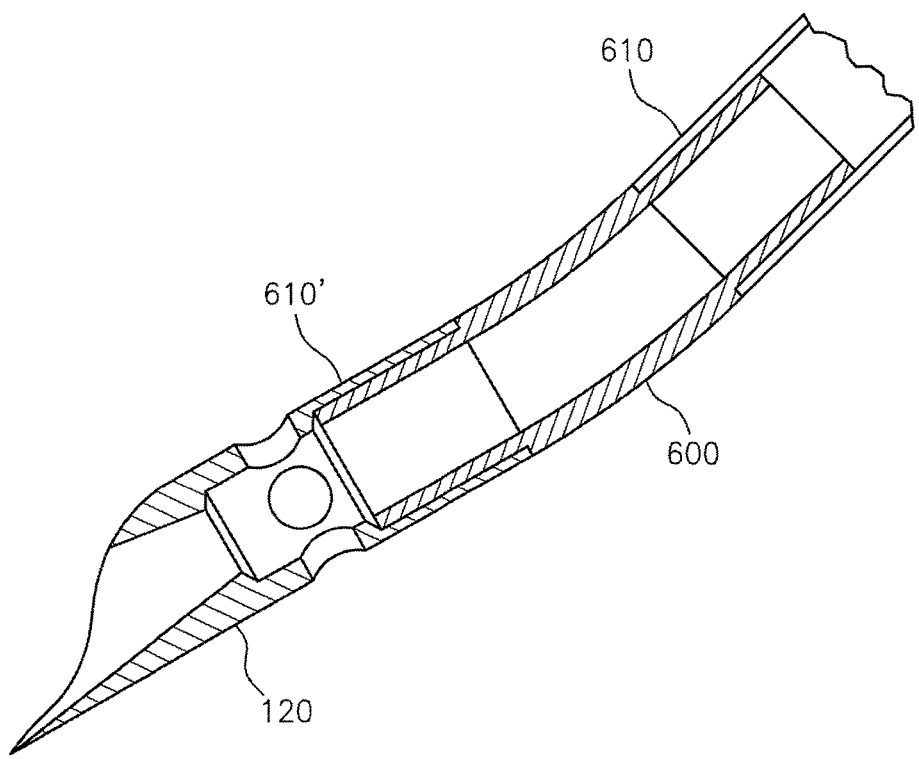
FIG. 16 is a schematic view of a coupler creating an angled bend in a conduit in accordance with an embodiment of the invention.

As noted above, a stand-off distance is defined by a distance that the distal region of the tissue interaction portion extends beyond the end of the waveguide. Accordingly, a laser beam guided by the waveguide assembly may be kept a consistent distance from target tissue. The stand-off distance in FIG. 10A is the sum of L1+L2. In some other designs, such as in FIG. 2A, the stand-off distance may be defined as essentially the length of the cantilevered distal end portion Referring again to FIG. 10B, in some embodiments, the distal tip may be coupled to a waveguide, with the aperture of the outlet being greater than or equal to a numerical aperture of the waveguide Referring to FIG. 16, a coupler 600 may also be used to create an angled bend in a conduit by joining two straight rigid cannulae 610, 610'.

Figure 17A:
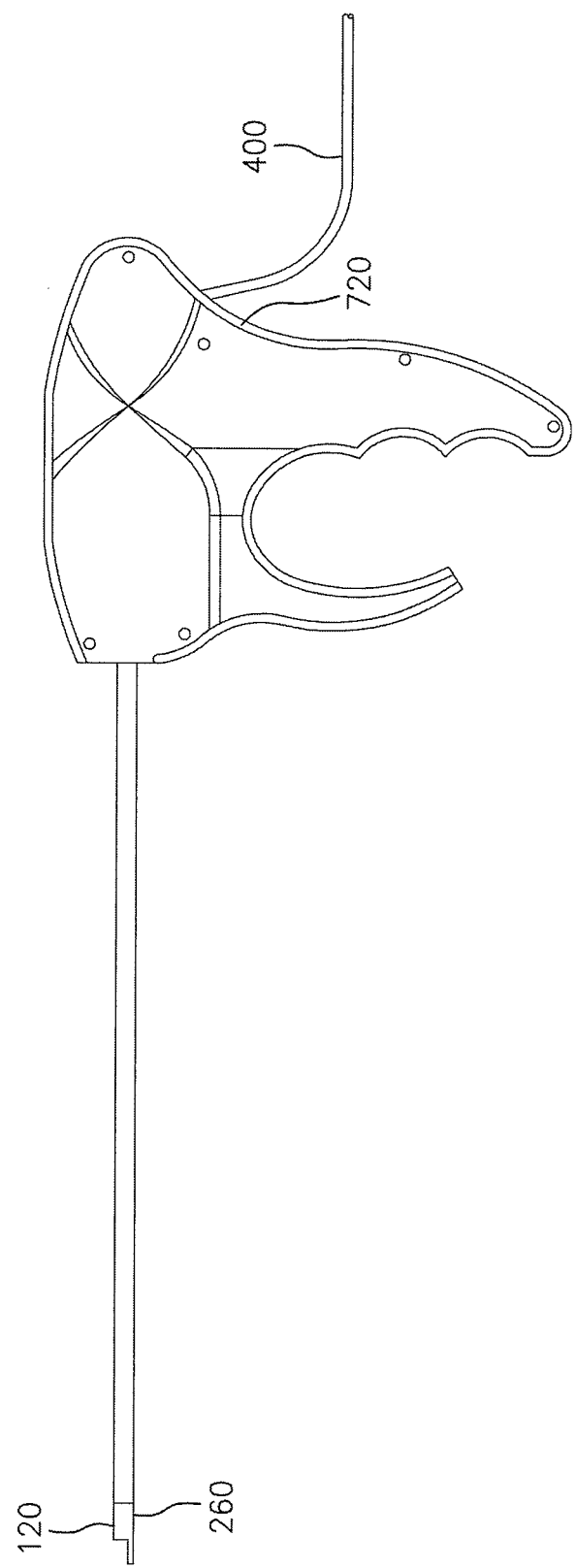
FIGS. 17A and 17B are schematic views of the cantilevered distal end portion of a distal tip interfaced to a force and/or distance feedback sensor in accordance with an embodiment of the invention.
Figure 17B:
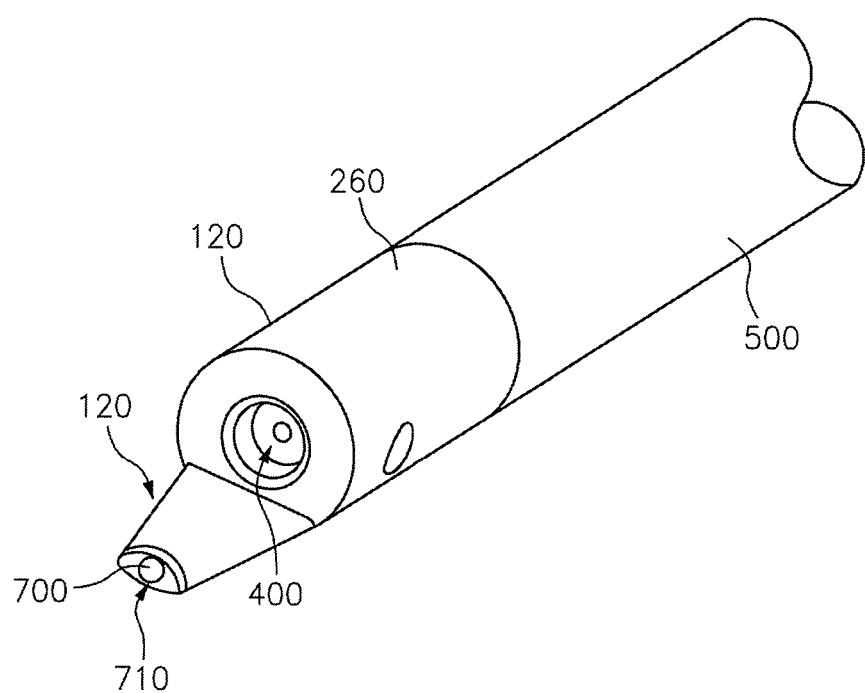

Referring to FIGS. 17A and 17B, the cantilevered distal end portion 260 may be interfaced to a force and/or distance feedback sensor 700 that may be used to adjust the distance of the waveguide from the tissue, or as an alert that the mechanical properties of the tissue have changed. For example, an underlying softer or harder tissue may be exposed following initial tissue ablation. An optical, mechanical, electric (e.g., resistance- or capacitance-based sensor) or electromechanical (e.g., piezoelectric force sensor) feedback sensor may be adapted to provide feedback to at least one of a robot or a computer interface. Examples of suitable sensing techniques may include optical coherent tomography [see e.g., Latour G., Georges G., Lamoine L. S., Deumié C., Conrath J., Hoffart L., "Human graft cornea and laser incisions imaging with micrometer scale resolution full-field optical coherence tomography," *J. Biomed. Opt.* 15(5), 056006 (2010) and Oh W. Y., Bouma B. E., Iftimia N., Yun S. H., Yelin R., Tearney G. J., "Ultrahigh-resolution full-field optical coherence microscopy using InGaAs camera," *Opt. Express* 14(2), 726-735 (2006)], acoustic sensing (U.S. Patent Publication No. 20070197895) or by using a piezoelectric transducer (see, e.g., U.S. Patent Publication No. 20080288031), incorporated herein by reference in their entireties.

As shown in FIGS. 17A and 17B, in an embodiment, the cantilevered distal end portion of the distal tip, e.g., a blunt dissection tip, may define a channel in which a sensor or part of a sensor may be placed. For example, a solid core optical waveguide 400 suitable for collecting signals for optical coherence tomography may be fed into the channel of the cantilevered distal end portion. An exposed front facet 710 of the optical waveguide 400, e.g., a $CO_2$ laser fiber, may be used to collect an optical signal that is guided by the waveguide/fiber placed in the conduit (for example along a channel in the wall of the conduit or attached to the wall of the conduit) to an optical sensor and readout 720.

Readout of the sensor may be integrated into the conduit, e.g., rigid conduit 500 (or flexible conduit 110), and may be connected to the sensor wirelessly or using separate wires or optical waveguides running along the conduit or waveguide. The readout may present a mini-display integrated in the conduit showing distance between distal end of the instrument and tissue. The readout may be present as a separate unit or be integrated with robotic display Referring to FIG. 18, some distal tips 120' may be designed without a specific tissue interaction region. An end portion 800 of the distal tip may be angled with a variable wall thickness to improve visualization and aiming. For example, a narrow distal portion can improve visualization of underlying tissue better (less blocking of the visual field) and can help to point laser radiation at the tissue.

Figure 19A:
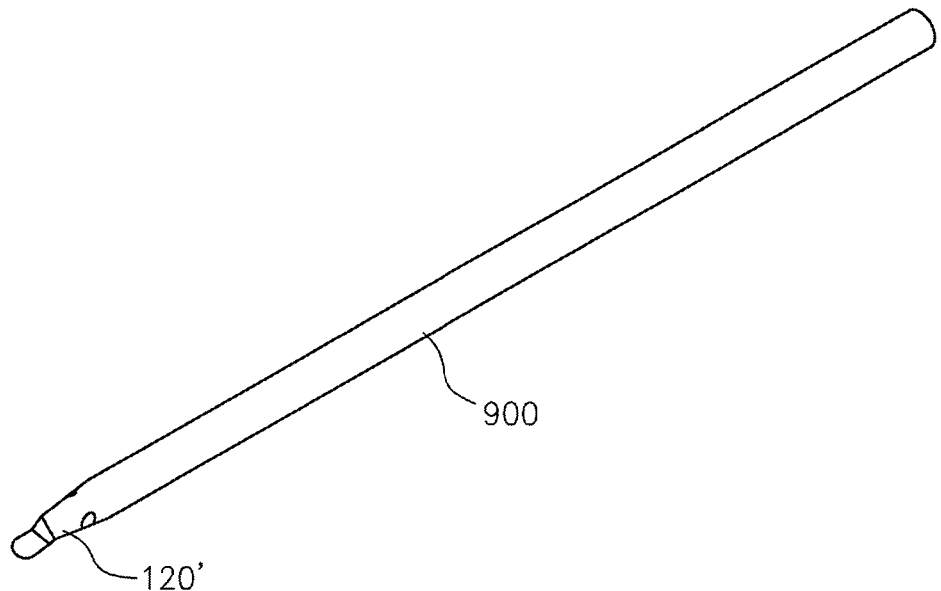
FIGS. 19A and 19B are schematic perspective and side-cross-sectional views of a distal tip formed from a portion of a conduit and integrated therein.
Figure 19B:
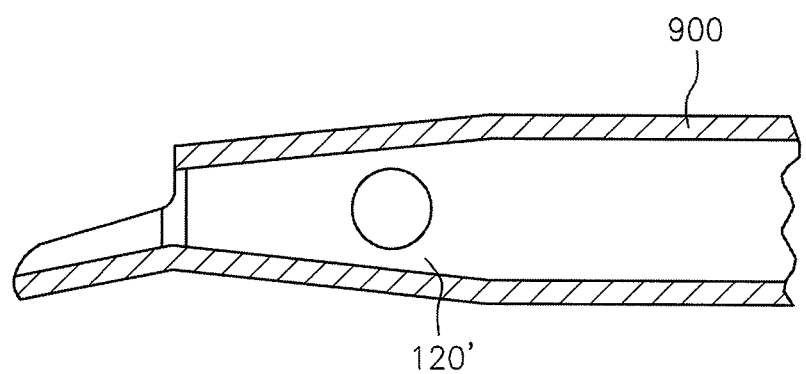

Referring to FIGS. 19A and 19B, a distal tip 120' may be defined in a conduit 900 (rigid or flexible), with the tip being formed from a portion of the conduit and integrated therein. In particular, the conduit may be an elongated hollow structure configured to receive a waveguide, a distal end portion of the structure defining (i) an inlet for receiving the waveguide therethrough; and (ii) an outlet aligned with the inlet adapted for (1) permitting egress of radiation from an output end of the waveguide and (2) abutting an end face of the waveguide, the outlet having a smaller diameter than a diameter of the inlet. The distal end portion may include a conical section and/or a cantilevered distal end portion. A waveguide may be disposed in the conduit. The conduit may include a gripping portion and a cannula portion.

Figure 20:
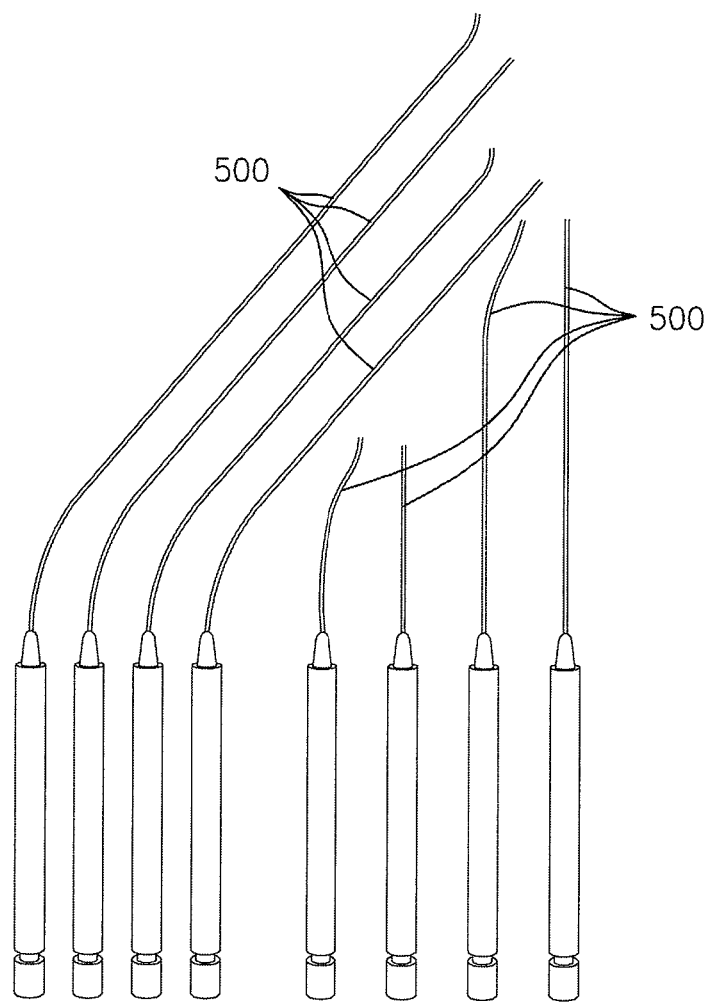
FIG. 20 are schematic views of a variety of rigid conduits suitable for use with embodiments of the invention.

Referring to FIG. 20, a typical rigid conduit 500 suitable for use with embodiments of the distal tips described herein may be straight or have multiple bends depending on the application, such as conduits from the ENT-HS handpiece set from OmniGuide. For example, conduits used for oral surgeries (e.g., base of tongue) are generally shorter and have fewer bends than conduits used for laryngeal or laparoscopic work. A typical range of bend radii for rigid cannulae are 5-90° (angle A) and total length (L) of the cannulae may be from 3 to 50 cm. A conduit may contain several bends placed anywhere between distal and proximal (adjacent to the handle) ends depending on the requirements of a particular application.

For laparoscopic applications, the bend radius on the distal portion of the conduit may be limited by the diameter of the laparoscopic opening, e.g., entry port in the trocar type device. For laparoscopic use it may be desirable to have the smallest possible entry port, therefore, an ability to bend the conduit after it slips through the trocar is desirable. This ability can be attained for example by having a control wire or push rod type mechanism to change distal bend radius. These types of mechanisms are common and can be easily implemented by someone of ordinary skill in art.

Traditional laparoscopic tooling generally consists of a rigid shaft with a working feature located on the distal tip, and a hand grip located proximally. The shaft is typically stainless steel with an outer diameter of industry standard sizes, commonly 3, 5, or 8 mm. These sizes may be desirable due to the requirement of the tool to pass through a pressure sealing device, such as a trocar, having an orifice of similar size. The length of the pressure sealing device varies, but typically does not fall below 4 inches.

Methods of Manufacturing

A surgical waveguide assembly, e.g., the assemblies shown in FIGS. 11A and 11B, may be formed as follows. A rigid conduit may be provided. A distal tip 120 or 120' may be attached to the rigid handpiece. The tip may be attached permanently by, e.g., gluing, brazing, welding, or soldering, or removably, e.g., by a threaded connection or an interference fit. A waveguide may be inserted into the rigid handpiece, for example manually. Examples of suitable commercially available waveguides are the OmniGuide ENT-L or BP-LE180 fibers.

A surgical waveguide assembly, e.g., the assembly shown in FIG. 12A, may be formed as follows. A flexible conduit 110 may be provided. A distal tip 120 or 120' may be attached to the flexible conduit. The tip may be attached permanently by, e.g., gluing, brazing, welding, or soldering, or removably, e.g., by a threaded connection or an interference fit. A waveguide may be inserted into the flexible conduit for example manually. An example of a suitable commercially available waveguide: OmniGuide ENT-L or BP-LE180 fibers. A surgical waveguide assembly, e.g., the assembly shown in FIG. 12A, may be formed as follows. A waveguide jacket 570 may be provided (for example polyimide tubing manufactured by Microlumen). A distal tip 120 or 120' may be attached to the waveguide jacket. The tip may be attached permanently by, e.g., gluing, brazing, welding, or soldering, or removably, e.g., by a threaded connection or an interference fit. A waveguide may be inserted into the flexible conduit. Examples of suitable commercially available waveguides are OmniGuide ENT-L or BP-LE180 fibers.

The waveguide conduit of FIGS. 19A and 19B, including a distal tip integrated with the waveguide conduit, may be formed as follows. An elongated hollow structure (rigid or flexible) configured to receive a waveguide may be provided (for example hypodermic stainless steel tubing available from New England Small Tube, or polyimide tubing available from Microlumen). The hollow structure may be a tube that may have a cylindrical, elliptical, square, or any other suitable cross-section. An end portion of the structure may be shaped to define (i) an inlet for receiving the waveguide therethrough; and (ii) an outlet aligned with the inlet adapted for (1) permitting egress of radiation from an output end of the waveguide and (2) abutting an end face of the waveguide, the outlet having a smaller diameter than a diameter of the inlet. The end portion may be shaped by at least one of machining, shaping (e.g., extrusion or swaging) or by adding material (e.g., 3D printing). The elongated structure can be made of stainless steel (e.g., 300 series stainless steel), titanium, or other medical grade metal. A wide range of polymer materials may be used as well, for example polyimides, silicones, PEEK, PES, and polycarbonates.

Use of Devices Employing Embodiments of the Invention

Laser radiation is a well-known modality, finding application in many modern medical procedures, including minimally invasive surgery involving laparoscopic approach as well as robotic systems. In such procedures the laser radiation is delivered to the target tissue by flexible optical waveguides. However, a number of limitations exist in how the waveguide may be introduced into a patient and manipulated inside to deliver laser energy to targeted tissue safely and precisely as well as with reliable control.

In order to overcome such limitations, a method of introducing a waveguide into a patient and controlling it inside the patient is devised, where a separate flexible conduit with certain mechanical properties and additional functionality at the tip is used. A suitable flexible conduit includes a distal tip providing an attachment function, a waveguide coupling function, and tissue aiming and handling function.

The attachment function may implemented by a grasper allowing the flexible conduit to be attached to and detached from, for example, a laparoscopic manipulator or robotic arm manipulator, at ease. This grasper may be a handle adapted to mate with the manipulator. This allows a surgeon to change instruments used with the manipulator at any given time, for example, changing manipulator usage from controlling the laser energy waveguide to controlling some other instrument.

The waveguide coupling function may be implemented by a distal tip having an inlet sized to receive the waveguide end and an outlet for the laser energy output, where the waveguide is aligned and kept fixed with respect to the flexible conduit during manipulation. Thus the flexible conduit distal tip may prevent any possible damage to the waveguide itself and allows manipulation of the waveguide output with precise control in order to deliver the laser energy to the target. In addition, the flexible conduit distal tip is a protector of the waveguide distal end against tissue interaction, such as fluid splashes, smoke and debris.

The tissue aiming and handling function may be implemented by means of the distal tip cantilevered distal end portion, which may be used for tissue manipulation, including blunt dissection, probing depth of tissue, performing general tissue handling, e.g., exposing fresh tissue to the laser beam or applying tension to the tissue during cutting. The cantilevered distal end portion is designed to align with the laser beam from the tip outlet and thus assists aiming of the laser beam to the precise location by means of tissue contact.

Figure 21:
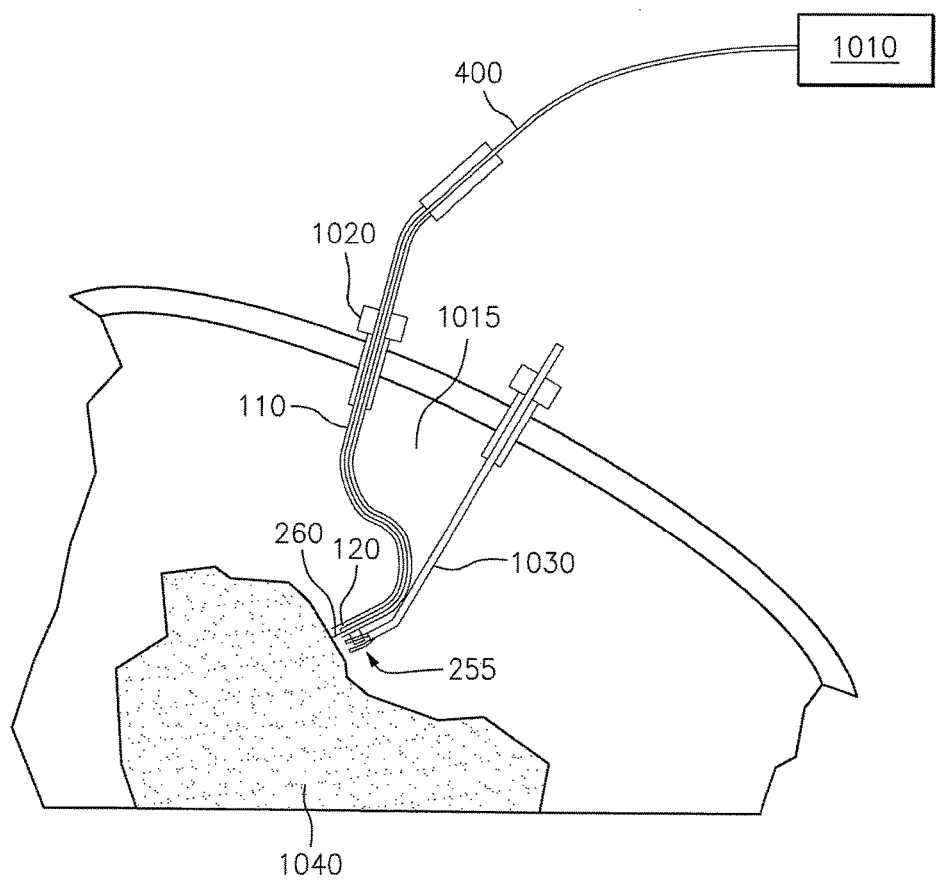
FIG. 21 is a schematic view illustrating a method for treating a patient with a laser and a flexible conduit, in accordance with an embodiment of the invention.

Referring to FIG. 21, a doctor may execute the following steps to treat a patient with a laser using a flexible conduit:
1. Introduce a waveguide 400 disposed in a flexible conduit with a distal tip 120, with the waveguide distal end being coupled to the distal tip of the flexible conduit and the waveguide proximal end being in communication with a laser system 1010, into a patient, e.g., into an abdominal cavity 1015, through a trocar 1020.
2. Grasp the flexible conduit distal tip with a manipulator tool 1030 (e.g., a robotic needle driver); this may be enabled by the distal tip having a reliable grasping mechanism, e.g., a handle adapted to mate with the manipulator.
3. Move the distal tip of the flexible conduit, and therefore the waveguide distal end, to the target tissue 1040 location.
4. Manipulate the tissue to better expose the treatment spot, with the flexible conduit distal tip providing protection of the waveguide distal end from any damage arising from manipulating the tissue mechanically.
5. Align the flexible conduit distal tip, and therefore the waveguide distal end, into correct position for firing laser. The doctor needs to be well aware of where the laser beam goes and how large the laser beam spot size is. This may not be possible without a contact mode that is enabled by the distal tip having a cantilevered distal end portion, and that may also be used to provide a preferred stand-off distance. The waveguide distal end preferably follows the manipulator without any slippage or wobbles. This may be enabled by a reliable grasping mechanism, as provided by the distal tip described herein, and reliable coupling of the waveguide distal end to the flexible conduit distal tip.
6. Fire the laser in the laser system 1010 and treat the target tissue while moving the waveguide distal end by moving the distal tip 120 of the flexible conduit. Precise aiming control and stability is needed. This may be enabled by having a reliable and steady grasper mechanism, e.g., a handle 255 on the distal tip 120 adapted to mate with the manipulator 1030; control of waveguide bending, e.g., with a preferentially bending jacket; and control of distance to the tissue, e.g., with the cantilevered distal end 260 of the distal tip 120.
7. Stop laser, move the waveguide distal end to point to another target location.
8. Poke at the tissue, move it around to expose the treatment spot better.
9. Assess a depth of an incision in the target tissue or dimensions of the target tissue using markings on the distal tip. As an example markings may be spaced 1-2 mm apart to provide a visual reference point for the user. As discussed above, such markings may provide additional feedback, with the visual indicator supplementing sensory indicators. Moreover, the markings may assist in the evaluation of the size of a feature or spot size of a laser beam, by providing an absolute reference for lateral and/or depth dimensions. An absolute reference may be desirable, in view of the magnified images provided by cameras during surgery.
10. Align waveguide distal end to the correct position for firing the laser, using a design of the cantilevered distal end of the distal tip to detect placement of the laser beam.
11. Fire the laser and treat the target tissue while moving the waveguide distal end.
12. Stop laser, move the waveguide distal end to point to another target location.
13. If necessary, release the waveguide by disengaging the flexible conduit distal tip from the manipulator, and use the manipulator tool for another task.
14. Grasp the flexible conduit distal tip with the manipulator tool to use the laser again.
15. Repeat again steps 3 to 11 at another target location, release the waveguide, perform another task with the manipulator, pick the waveguide up again, treat more tissue with the laser, etc.

The length of the cantilevered end portion of the distal tip may be adjusted, thereby adjusting the predetermined stand-off distance for tissue treatment. The length may be adjusted manually or by a computer-controlled interface or by a mechanical manipulator.

Figure 22:
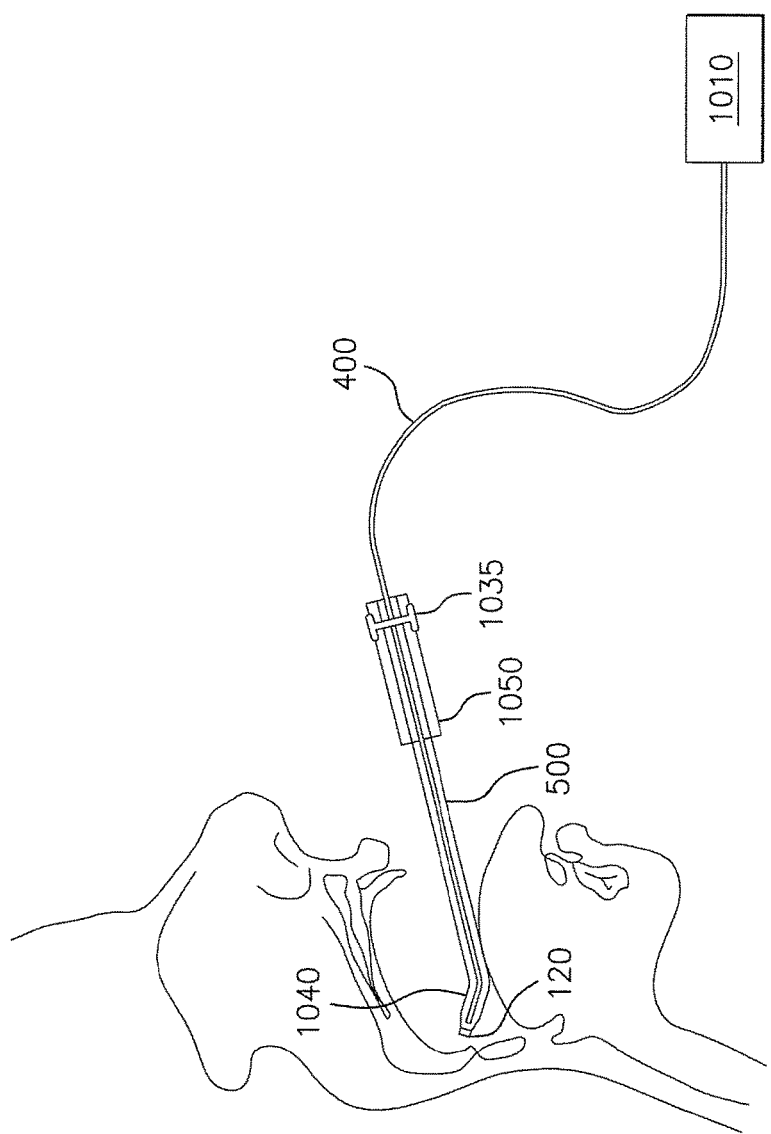
FIG. 22 is a schematic view illustrating a method for treating a patient with a laser and a rigid conduit, in accordance with an embodiment of the invention.

Referring to FIG. 22, a doctor may execute the following steps to treat a patient with a laser using a rigid conduit:

1. Introduce a waveguide 400 disposed in a rigid conduit 500 with a distal tip 120, with the waveguide distal end being coupled to the distal tip of the rigid conduit, into a patient through a natural opening such as a mouth or an ear without a trocar. The rigid conduit may also be introduced into the patient e.g., into an abdominal cavity, through a trocar. The waveguide 400 may be locked in place by a waveguide lock 1035 at a proximal end of the rigid conduit.
2. Grasp the rigid conduit, e.g., by a handle 1050 of the rigid conduit, by hand or a robotic manipulator.
3. Move the distal tip of the rigid conduit, and therefore the waveguide distal end, to the target location.
4. Manipulate the tissue to better expose the treatment spot, with the rigid conduit distal tip providing protection of the waveguide distal end from any damage arising from manipulating the tissue mechanically.
5. Align the rigid conduit distal tip, and therefore the waveguide distal end, into correct position for firing the laser. The doctor needs to be well aware of where the laser beam goes and how large the laser beam spot size is. This may not be possible without a contact mode that is enabled by the distal tip having a cantilevered distal end portion, and that may also be used to provide a preferred stand-off distance.
6. Fire the laser and treat the target tissue while moving the waveguide distal end by moving the distal tip of the rigid conduit, as precise aiming control is needed. This may be enabled by controlling the distance to the tissue, e.g., with the cantilevered end of the distal tip.
7. Stop the laser, move the waveguide distal end to point to another target location.
8. Poke at the tissue, move it around to expose the treatment spot better.
9. Assess a depth of an incision in the target tissue or dimensions of the target tissue using markings on the distal tip. As an example markings may be spaced 1-2 mm apart to provide a visual reference point for the user.
10. Align the waveguide distal end to the correct position for firing the laser, using a design of the cantilevered end of the distal tip to detect placement of the laser beam.
11. Fire the laser and treat the target tissue while moving the waveguide distal end.
12. Stop laser, move the waveguide distal end to point to another target location.
13. Repeat again steps 3 to 11 at another target location.

Preferentially Bending Jacket

A waveguide may have one or more structural asymmetries. For example, a waveguide may have a spiral multilayer structure, due to the manufacturing process used to form the waveguide. See, e.g., U.S. Pat. Nos. 7,167,622; 7,311,962; and 7,272,285. A structural discontinuity may be present in the form of a seam along the waveguide length. This seam may be created by the termination of a spiral wrap mirror structure at the outer surface of a hollow core of the waveguide, the core being disposed along a length of the waveguide. This seam is a discontinuity, i.e., a defect in the waveguide mirror structure, and may affect optical bend losses in the waveguide.

Figure 23A:
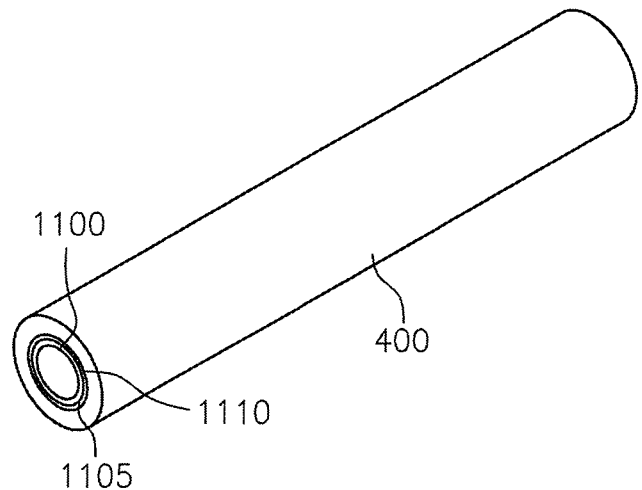
FIGS. 23-24 are perspective views illustrating the positioning of radiation in a straight and a bent waveguide core, with FIG. 23a being a perspective view of a straight waveguide, FIG. 23b being a perspective view of a bent waveguide, and FIG. 24 being a perspective view of a bent waveguide with a seam located out of the bending plane.
Figure 23B:
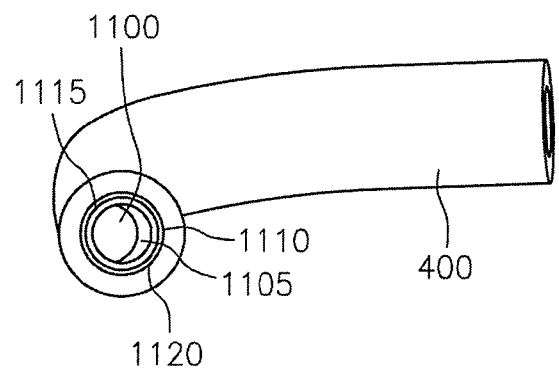

Referring to FIG. 23, when the waveguide 400 is not straight but bent, the radiation intensity 1100 distribution of the propagating light in the core, e.g., waveguide hollow core 1105 within a mirror structure 1110, may change so that the amount of radiation leaking out of the waveguide core into the mirror structure may increase on the outer side 1115 of the waveguide bend and decrease on the inner side 1120 of the waveguide bend. The amount of radiation leaking into the mirror above and below the bend may remain about the same as for a straight waveguide.

Figure 24:
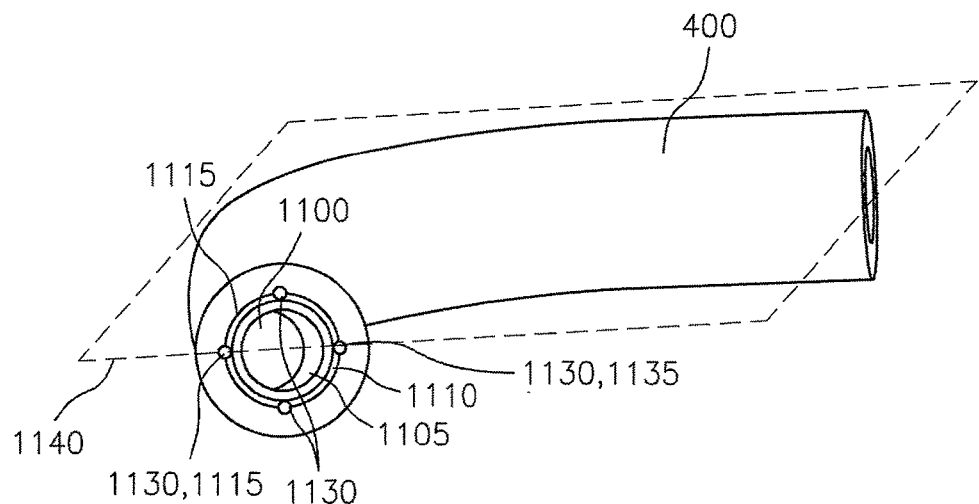

Referring to FIG. 24, it is therefore advantageous to control seam 1130 orientation with respect to the waveguide bending such way that preferably the seam is always on the inner side 1135 of the bend, or at least out of the bending plane 1140.

Preventing the seam from being located on the outside 1115 of the bend when the waveguide is bent thus improves the waveguide performance and reliability. One way to control seam orientation is to alter the cylindrical symmetry of the waveguide mechanical properties such that the waveguide 400, e.g., disposed in jacket 570, preferentially bends in one plane and places the spiral mirror structure seam out of the preferential bending plane at 90 degrees orientation, such as shown in FIG. 24. It should be noted that the preferential bending of the waveguide does not greatly reduce the positioning ability of the whole waveguide, because a waveguide can easily twist in case of multiple bends while maintaining certain orientation of the seam. Another way to control seam orientation is to encase the waveguide in a protective tube, i.e., a waveguide jacket 570 that bends preferentially. A suitable tube bends much more easily in one plane than in an orthogonal plane, i.e., than in a plane disposed at a 90 degree angle to the preferred plane. Using such waveguide jacket and fixing the waveguide seam to be oriented at 90 degrees to the jacket's preferential bending plane reduces the probability that the seam is disposed on the outside of the bend during usage involving waveguide bending. Preferential bending of the jacket does not greatly hinder positioning of the waveguide because the jacket with the waveguide inside can easily twist, even when multiple bends are formed, while maintaining the preferred orientation of the seam. In general, the jacket may also provide additional mechanical strength, and increase overall safety and reliability of the device. Different jacket designs may be used to control other mechanical properties of the device over its length, such as flexibility characteristics.

In an embodiment, the jacket may include two wires disposed along the length of the jacket, and placed at 180° with respect to each other. The bend plane may be defined at 90° to the plane defined by the two wires when the jacket is in a linear configuration.

Figure 25A:
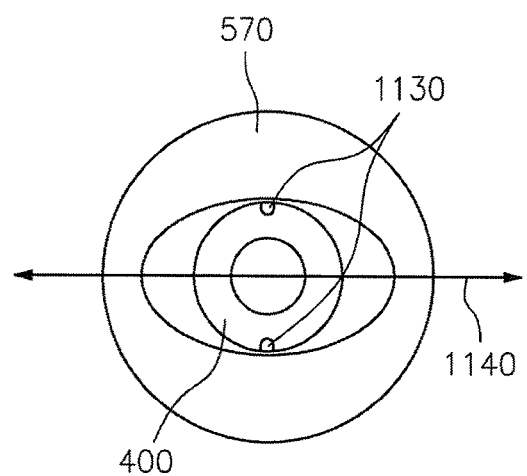
FIGS. 25A-25D are cross-sectional views illustrating the creation of a bend plane in a waveguide by use of asymmetric jackets.
Figure 25B:
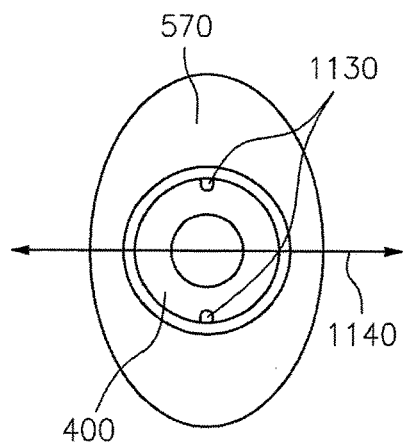
Figure 25C:
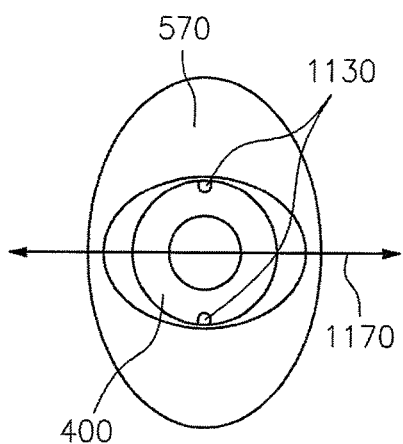
Figure 25D:
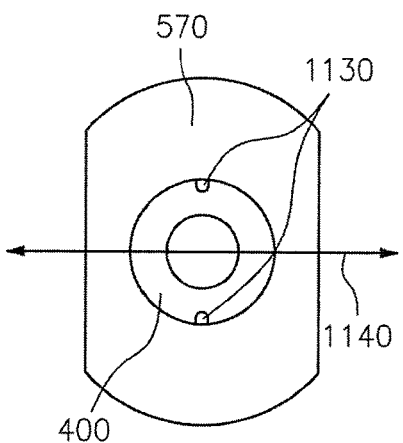

Preferentially bending jackets may be made by breaking down the cylindrical symmetry of the mechanical properties of a jacket. This may be achieved by a number of ways. One way, for example, is to change the shape (cross-section) of the jacket as illustrated in FIGS. 25A-25D, which illustrate different jacket cross-sections. A suitable jacket 570 may be have a round outer surface and an oval inner surface (FIG. 25A), an oval outer surface and a round inner surface (FIG. 25B) or both inner and outer surfaces may be oval (FIG. 25C). The oval shapes do not have to be strictly elliptical but may be achieved by flattened sections such as shown in FIG. 25D, where the jacket has flat sides on the outer surface. In some embodiments, the jacket may have flat sides on the inside surface. In still other embodiments, the jacket may have flat sides on both the inside and outside surfaces.

The waveguide seam is preferably fixed in one of two possible locations 90° from the preferential bending plane 1140. The waveguide may be maintained in a position having a fixed seam orientation with respect to the jacket by means of adhesive applied between the jacket and the waveguide at one or more locations along the length.

Figure 26:
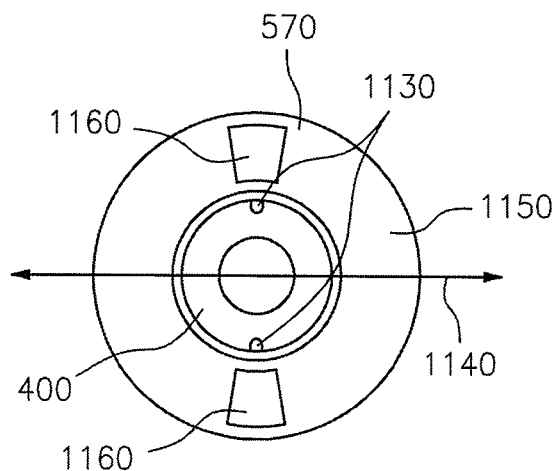
FIGS. 26, 27A, and 27B are cross-sectional views illustrating the creation of a bend plane in a waveguide by incorporating high modulus material into a jacket, in accordance with an embodiment of the invention.

Alternatively, composite materials may be used to construct the jacket with an asymmetric distribution of higher elastic modulus (higher Young's modulus) and lower elastic modulus materials. Referring to FIG. 26, a jacket 570 wall may include a material 1150 having a lower Young's modulus. First and second regions may be defined in the jacket and extend along at least a portion of a length of the jacket. The first and second regions may be disposed opposite each other along a diagonal of the cylindrical jacket, and at least one of the first and second regions may include a second material 1160 having a second Young's modulus higher than the first Young's modulus material. The second material may be incorporated into the jacket wall. The first and second regions create a preferential bending plane orthogonal to the diagonal.

In a preferred embodiment, the jacket wall may be made from plastic material and may have metallic wires incorporated into the jacket wall and located opposite each other on the jacket wall circumference. Suitable plastic materials include polyesters (e.g., Hytrel® thermoplastic plastic elastomer), polyamides (e.g., nylon), polyether block amides (e.g., Pebax®), polyether ketones (e.g., "PEEK"), polyether sulphones, polyether imides, polyimides, polyethylenes, and/or polyurethanes. The metallic wires may include metals and metallic alloys such as titanium, copper, aluminum, stainless steel, nitinol, nickel, constantan, and/or nichrome. Alternatively, the higher tensile material may also be plastic, such as aramid fibers (e.g., Kevlar® aramid fiber). The jacket may also be made of whole metal tubing or wholly from braided, twisted or coiled metal wires.

In some embodiments, the first material may have a higher Young's modulus than the second material.

A preferred range for the elastic modulus for the jacket wall is from 0.15 GPa to 5 GPa, preferably about 2.5 GPa. These values ensure flexibility and strength of the jacket with a thin wall having a thickness less than 0.5 mm, such as 0.06 mm, 0.08 mm, 0.1 mm, 0.14 mm, 0.16 mm, 0.18 mm, or 0.2 mm. A preferred range for the elastic modulus of the higher modulus materials, e.g., wires, is 50 GPa to 500 GPa, more preferably about 150 GPa and higher, to achieve preferential bending properties within the constraints of the thin wall requiring the use of thin wires or fibers.

The proper materials arrangement may be achieved by co-extrusion of jacket tubing materials.

The cylindrical jacket may define an opening sized to receive a waveguide. The opening may have a diameter selected from a range of, e.g., 0.2 mm to 1.8 mm.

In use, the waveguide may be maintained in a position having a fixed seam orientation with respect to the jacket in one of two possible locations 90° from the preferential bending plane. This may be achieved by applying adhesive between the jacket and the waveguide at one or more locations along a length of the jacket.

Figure 27A:
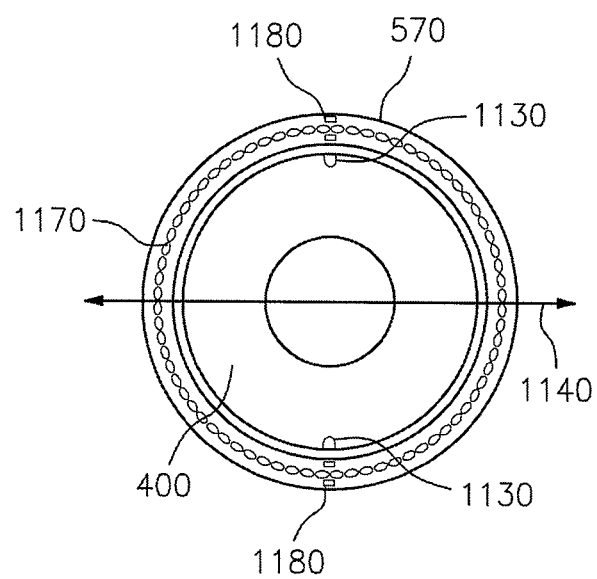
Figure 27B:
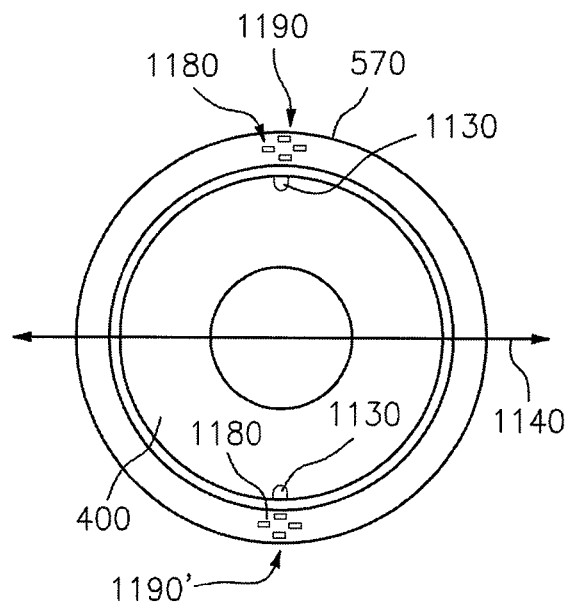

Referring to FIGS. 27A-27B, the jacket 570 may contain a strength member in the wall, such as a metallic wire braid 1170. An example of braid-reinforced plastic tubing suitable for such jackets is available commercially from Microlumen Inc., based in Oldsmar, Fla. The braid strands count and braid picks per unit length as well as the wire cross-section and wire size determine the flexibility characteristics and kink-resistance of the braid. Rectangular cross-section flat wires typically enable more rigid and kink resistant braid within a given wall thickness than round wires. A higher number of picks per unit length gives better flexibility and kink resistance while a lower number of picks per unit length increases rigidity. In an embodiment, a jacket may use braid-reinforced polyimide tubing that has a braid made with flat stainless steel wires 0.0005"×0.003" with 90 picks per inch. In some embodiments, the preferentially bending jacket may be fabricated by incorporating two or more axial wires 1180 in addition to a metallic braid. Using thin metallic wires to control jacket mechanical properties may be a preferred solution when there is a limitation on the wall thickness of the jacket. FIG. 27A shows the cross-section of a jacket that has a metallic wire braid 1170 in its wall, and two axial wires 1180 are intertwined into the braid and embedded into the jacket wall. The axial wires may be a similar size as the wires used in the braid, or thicker. The wires may have one of many different cross-sections, such as round, rectangular, or square. A preferred embodiment utilizes flat (rectangular) stainless steel wires 0.0005"×0.005" that are intertwined into the braid. In some embodiments, instead of two individual axial wires located opposite each other across the center of the jacket, two groups of axial wires may be used, with the groups located opposite each other across the center of the jacket and each group containing two or more axial wires.

Referring to FIG. 27B, in another embodiment, a jacket may not include a wire braid, but rather may include axial wires running along the length of the jacket in two groups 1190, 1190'. Each of the two groups may include a single wire or a plurality of wires, e.g., 2 wires or more, 3 wires or more, or 4 wires or more. The wires may be of different sizes and shapes (e.g., round, square, or rectangular) and arranged in different patterns. For example, groups of 3 round wires, each with a 0.001" diameter, may be arranged side by side along the circumference of the jacket wall and intertwined into the braid.

The wires in the preferentially bending jacket may be made of metal, e.g., stainless steel. In some embodiments, the wires may be made from other materials having a high tensile elastic modulus, for example, Kevlar cords or glass fibers may be used for axial wires. Preferably, the tensile elastic modulus of the wires is at least 150 GPa.

In a preferred embodiment, the preferentially bending jacket may be made of polyimide tubing with a braid and two axial wires. The jacket wall thickness may range from as thin as 0.08 mm to as thick as 0.25 mm, preferably 0.18 mm. The jacket may define an opening sized to receive an optical waveguide. Accordingly, the jacket may define an opening having a diameter selected from a range of, e.g., 0.2 mm to 1.8 mm.

Generally, dimensional constraints on the finished device and designed mechanical properties determine the specification of the wall thickness. Thinner wall jacket are more flexible while added wall thickness results in more rigid and kink-resistant jackets. The metallic braid may be made of stainless steel rectangular cross-section wires having dimensions of 0.0127 mm×0.076 mm or thicker wires with dimensions of 0.025 mm×0.076 mm or 0.025 mm×0.127 mm. Two axial wires may run along the jacket length and be intertwined into the braid, the axial wires being of the same size and cross-section as the wires used in the braid. In a preferred embodiment, the axial wires may have a cross-section of 0.0127 mm×0.1778 mm. Methods for making a jacket that includes a braid encased in polyimide are well known to those of ordinary skill in the art; for example, braid-reinforced polyimide tubing is available commercially, from, e.g., Microlumen Inc. Similar methods may be used to form the preferentially bending jacket of the invention, with the addition of intertwining axial wires into the braid prior to coating the braid with polymer.

In some embodiments, a preferentially bending jacket may be used with a multilumen (multi core) waveguide that combines several functionalities, e.g., guiding radiation of several different wavelengths or using other lumens for optical imaging. In this case, control of the position of the lumens may be important to the application. For example, different lumens may be used for in-situ chemical analysis (e.g., taking gas samples, or optical analysis of tissue) or to guide different wavelengths (e.g., one for cutting the tissue, another one for coagulating blood). The use of the preferentially bending jacket described herein with the multilumen waveguide allows selective positioning of the lumens.

Waveguide Tip for Attachment to Waveguide, a Waveguide Jacket, or a Waveguide Assembly Conduit For protection, a flexible waveguide may be enclosed in a flexible jacket extending from the proximal end of the device to the distal end. Protection of the waveguide distal end may also be achieved by employing specialized waveguide distal tips such as secondary waveguides attached to the end of main waveguide. Examples of such tips are disclosed in PCT publication WO 2011/075442, incorporated herein by reference in its entirety. Material selection criteria for tips that are also waveguides is discussed in PCT publication WO 2011/075442. Material choices for waveguiding tips may be limited by optical constraints.

Embodiments of the invention include waveguide tips for the protection of waveguide ends that may or may not guide the laser radiation, and that allow unobstructed propagation of the laser beam out of the waveguide. Such waveguide tips may have more complex shapes than a simple sleeve over the waveguide, depending on the waveguide dimensions, waveguide core diameter, laser beam divergence, and waveguide protective jacket dimensions. In some embodiments, the waveguide tips may be used to manipulate tissue mechanically without danger of damaging the optical waveguide end facet. Smaller waveguide tip profiles (e.g., relatively small outside diameter) provide better visualization of the target spot at the tip of the device and greater surgical precision, as well as easier insertion into delivery tools. Waveguide tips may be waveguiding as, for example, described in, e.g., PCT publication WO 2011/075442. Waveguiding tips may be made of, e.g., silica with silver and silver iodide coating in the interior. In case of non-waveguiding tips, a much wider range of materials may be suitable for making such tips, since optics for guiding of radiation does not have to be considered. These materials may be, for example, metals and metal alloys such as titanium, stainless steel, or silver, or ceramic such as alumina or zirconia.

Figure 28:
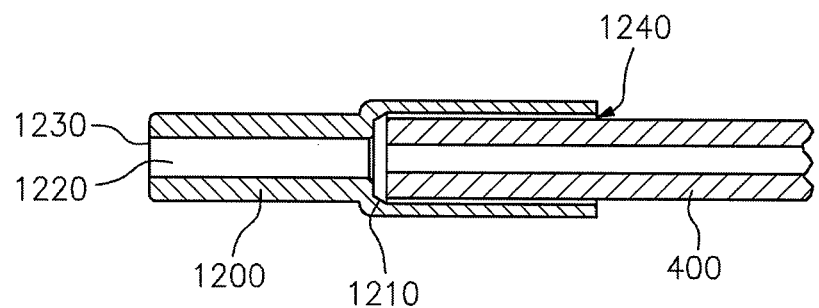
FIGS. 28-33 are cross-sectional views illustrating waveguide tips, in accordance with embodiments of the invention.

Similarly, an important design aspect of a non-waveguiding waveguide tip is the distal opening. To increase waveguide protection against tissue debris, fluid splashes, and backscattered radiation, the waveguide tip preferably has a distal opening with a distal outlet that is just large enough to allow laser radiation output and not any larger. Therefore, precise alignment of the waveguide tip to the waveguide may be desired to ensure concentricity of the waveguide core and the waveguide tip distal opening. Referring to FIG. 28, one way to achieve this is by employing a design that automatically centers the waveguide tip 1200 to the waveguide 400 by including a conical feature 1210 on an inner surface of the waveguide tip. The illustrated waveguide tip has inside a narrow distal portion defining a distal opening 1220 leading to a distal outlet 1230 at a distal end. The narrow distal portion inside the waveguide tip widens at a proximal end, and transitions to a wide proximal portion, with a transitional region between the narrow distal portion and the wide proximal portion defining a conical feature. The wide proximal portion includes a proximal opening 1240 sized to fit snugly over an end of a waveguide. In preferred embodiments the narrow distal portion inside the tip is at least 0.1 mm in diameter, e.g., 0.2 mm in diameter, 0.45 mm in diameter, or 0.55 mm in diameter, or 0.65 mm in diameter, or 0.75 mm in diameter or 0.85 mm or larger. The proximal portion inside the tip is at least 0.2 mm in diameter, e.g., 0.4 mm in diameter, 0.65 mm in diameter, or 0.75 mm in diameter, or 0.85 mm in diameter, or 1 mm in diameter, or 1.1 mm in diameter or larger. The distal outlet at an end of the distal opening is aligned with the proximal opening, and is adapted for permitting egress of radiation from an output end of the waveguide. The conical feature for waveguide tip-to-waveguide alignment allows centering the waveguide to the waveguide tip within a range of waveguide outer diameters determined by manufacturing tolerances that may be as large as ±5%.

In an embodiment, the waveguide tip is centered to the waveguide by a conical feature and may be attached to the waveguide by an adhesive. Suitable adhesives include one part or two part epoxies and glues that are heat-curable or light-curable, e.g., Loctite 4013 UV-light curable adhesive, available from Henkel AG & Co., based in Duesseldorf, Germany, or Epotek 301, available from Epoxy Technology, Inc., based in Billerica, Mass. Fast cure adhesives such as UV-light curable are preferable to allow a quick assembly process.

Figure 29:
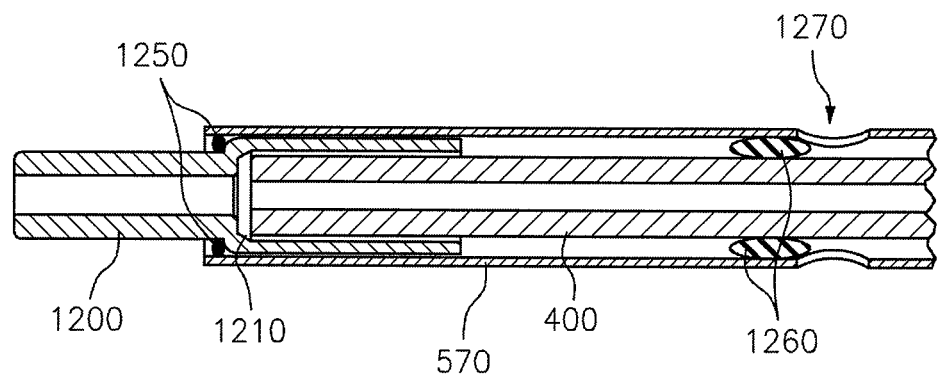

In another embodiment, the waveguide tip is not attached to the waveguide, but rather is attached to the jacket 570 that encloses the waveguide 400, as illustrated in FIG. 29. Accordingly, an outer diameter of the wide proximal portion is sized to fit inside a jacket, contacting an inner surface of the jacket, the outer diameter being, e.g., 1.14 mm. The waveguide tip 1200 and the waveguide 400 may both be held in place and attached to the jacket 570 by adhesive 1250, 1260. In case of metallic jacket, the tip can be welded to the jacket prior to inserting a waveguide into the jacket. Adhesive 1250 may be applied to the waveguide in one or more locations. In a preferred embodiment Loctite 4013 UV-light curable adhesive may be used. The jacket may define one or more holes 1270 for adhesive application during the assembly process. The waveguide tip may be attached to the waveguide jacket by a high temperature high strength adhesive 1250 (e.g., EPO-TEK 353ND epoxy, available from Epoxy Technology, Inc.) to ensure mechanical strength and reliability of the finished device.

Using a waveguide jacket with an optical waveguide provides a number of advantages. This includes the ability to separate the requirements of optical properties and manufacturability of the optical waveguide (which limit the choice of materials for the waveguide) from the mechanical requirements of the finished device. The latter may be provided by the jacket with a wide choice of available materials and jacket structural designs, for example, as in preferentially bending jackets. In addition, the waveguide jacket may provide additional protection against unwanted mechanical or optical failures. Finally, attaching both the waveguide tip and the waveguide to the jacket has an advantage of allowing a greater number of options for the geometrical configurations of the waveguide tip and jacket.

Figure 30:
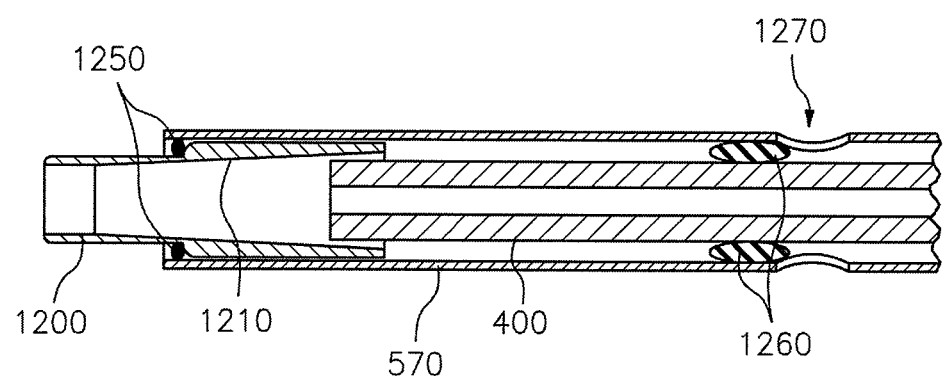

Referring also to FIG. 30, a preferred embodiment of the waveguide tip includes attachment of the waveguide tip to the jacket, the waveguide tip having an elongated conical feature 1210. The conical feature may be extended for easier alignment during the assembly process. For example, the conical portion may be sized such that the a distal end of the waveguide is disposed a fixed predetermined distance from a distal end of the device, e.g., at least 1.0 mm from a distal end of the device, e.g., 2.0 mm from a distal end of the device, or 3.0 mm from the distal end of the device, or 4.0 mm from the distal end of the device, or more.

Waveguiding waveguide tips may be used to limit beam divergence, thus reducing spot size and tip outer diameter, which aids in visualization. Smaller spot sizes may be preferred for otology procedures, and some neural and spine procedures. Waveguiding waveguide tips can also have bends that direct the laser beam into difficult to access anatomical structures.

Figure 31A:
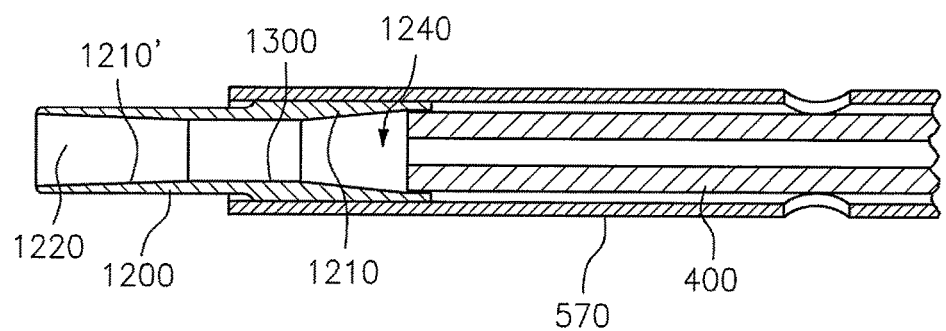
Figure 31B:
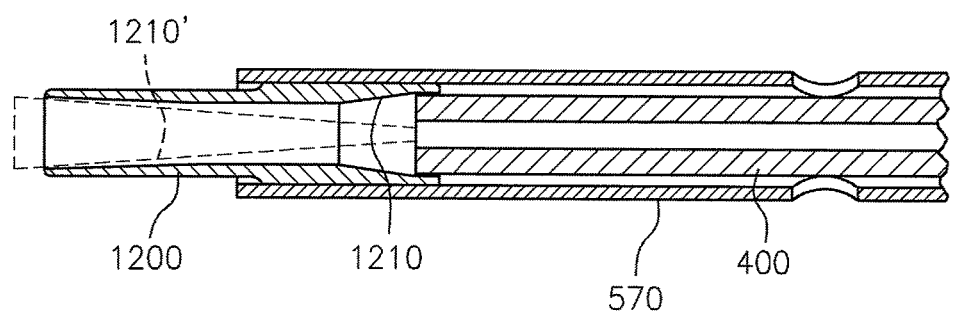

Different geometrical configurations of the waveguide tip may be employed to make a longer waveguide tip that allows for some laser beam expansion as the beam propagates through the waveguide tip. For example FIG. 31A shows the cross-section of the distal portion of the device, where the waveguide tip 1200 has two conical features 1210, a first proximal conical feature 1210 for alignment to the waveguide and for fitting over an end of the waveguide, and a second distal conical feature 1210' for allowing laser beam expansion and permitting egress of radiation from an output end of the waveguide. The waveguide tip may have a cylindrical portion 1300 between the conical features, or may have the first and second conical features 1210, 1210' abutting each other, as shown in cross-sectional view of the distal portion of the device in FIG. 31B. This design may be used to form a waveguiding waveguide tip which allows the use of a relatively smaller distal opening, spot size and outer diameter than if a nonwaveguiding tip had been used, and also allows laser beam propagation with some expansion, enabling the provision of a larger spot size at the distal end. The waveguide tip and the waveguide may be attached to the jacket by adhesives in the same way as described above and shown in FIGS. 29 and 30.

The tip dimensions, preferred output laser beam, and the divergence angle are determined by various tool requirements. In a preferred embodiment, the laser beam diameter at the waveguide output may be 0.30 mm, beam divergence full angle may be about 10 degrees, and the cone angle may be at least 10 degrees, with the distal opening diameter being at least 0.3 mm, e.g., 0.45 mm, or 0.55 mm or 0.65 mm or larger. The length of the distal portion of the tip with a beam expansion cone is preferably at least 3 mm, e.g., 4 mm or 5 mm or 6 mm, where cylindrical section is at least 0.5 mm, e.g., 1 mm or 2 mm or 3 mm in length.

Figure 32:
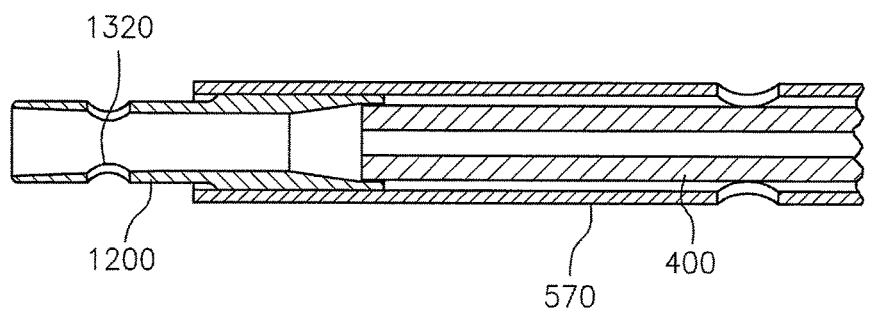

Referring to FIG. 32, the waveguide tip may have one or more side holes 1320. This configuration may be advantageous when gas flows through the waveguide core during use. Gas flow may be used for clearing tissue debris and blood during tissue cutting, for cooling the waveguide, and for therapeutic reasons such as assisting tissue coagulation. Side holes in the tip may provide an alternative route for the gas flow if the device is pressed against a target. The size of the side holes may be chosen such that a total cross-sectional area of the holes is at least twice the cross-sectional area of the waveguide core when r gas pressure relief is desired. Alternately, in some embodiments, higher gas pressure and or other fluid pressure may be desired. The holes may be placed close to the distal end of the tip or further away from the tip as long as they are not closed by the jacket. Placing holes further away from the tip allows gas pressure and flow relief for deeper insertion of the tip into the tissue. In a preferred embodiment, the holes are located 1.0 mm from the distal end of the tip and are 0.5 mm in diameter.

Figure 33:
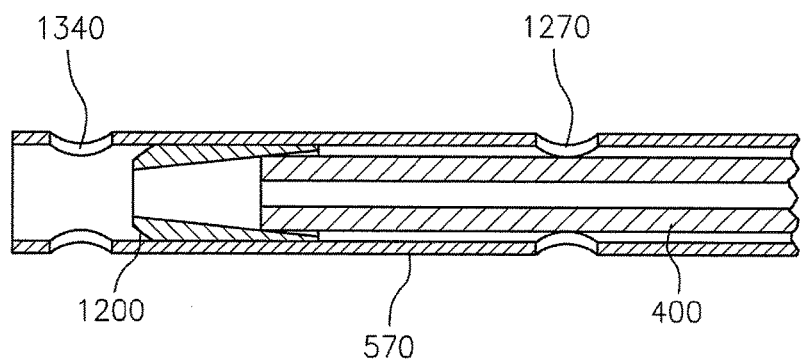

Referring to FIG. 33, the waveguide tip may be recessed in the jacket and holes 1340 made in the jacket in front of the distal tip for applications in which gas flow through the device is required even when the device distal end is pressed against a target. For assembly of the device, adhesive for attaching the waveguide tip to the jacket may be applied either through the jacket opening or through the jacket side holes 1270 by an adhesive dispenser through a properly sized dispensing needle. For example, a suitable adhesive dispenser system is the Ultimus series of dispensers, available commercially from Nordson Corporation, based in Westlake, Ohio.

In all of the above embodiments of the device with non-waveguiding waveguide tips, a waveguiding waveguide tip may also be employed. For example, waveguide tips silver-coated on the inside or waveguide tips with metallic silver and dielectric coating on the inside may be used. Waveguide tips may be made from a metal such as silver and have a dielectric coating for waveguiding properties. Alternatively, ceramic tips made of ceramics with appropriate optical properties may be utilized. Ceramic tips of complex shapes may be produced by extrusion process, grinding, or molding. The molding process allows the fabrication of complex shapes of ceramics with high precision. Suitable materials and coatings for introducing wave-guiding action to the tip are disclosed in, e.g., PCT publication WO 2011/075442. For example, ceramic tips with an inside coating of silver are useful in otology procedures.

The waveguide tip has been discussed above with respect to attachment to a waveguide or a waveguide jacket. In some alternative embodiments, the disclosed waveguide tips may be attached to a waveguide assembly conduit, e.g., a conduit such as a flexible conduit.

While there may have been described certain embodiments, it should be understood that the various features and functions of the invention may be used in various combinations and permutations. Sizes, materials, and the like are described by way of example only and are not to be considered limiting. The invention is to be defined by the meaning of the attached claims, including all equivalents.

What is claimed is:
1. A surgical device, comprising:
a waveguide conduit; and
a distal tip physically coupled to a distal end of the waveguide conduit, the distal tip including:
 a proximal opening having a first inner perimeter dimension, the waveguide conduit positioned in the proximal opening;
 an inlet communicatively coupled to the proximal opening, the inlet having a second inner perimeter dimension that is smaller than the first inner perimeter dimension;
 a first planar surface that forms an interface between the proximal opening and the inlet, the waveguide conduit in direct contact with the first planar surface;
 an outlet communicatively coupled to and aligned with the inlet, the outlet having a third inner perimeter dimension that is smaller than the second inner perimeter dimension of the inlet;
 a second planar surface that forms an interface between the inlet and the outlet; and a handle having a frame and an angled opening, which angled opening extends through the frame along a first axis, wherein the waveguide conduit and the inlet of the distal tip together define a waveguide passage through which a physical waveguide is passable, which waveguide passage extends along a second axis that is transverse to the first axis.

2. The surgical device of claim 1, the distal tip further including a cantilevered distal extension that extends beyond a distal end of the outlet.

3. The surgical device of claim 2, wherein the cantilevered distal extension has a flat surface adjacent to the outlet.

4. A surgical device, comprising:
   a waveguide conduit; and
   a distal tip, including:
      a proximal opening having a first inner perimeter dimension, the waveguide conduit positioned in and physically coupled to the proximal opening;
      an inlet communicatively coupled to the proximal opening, the inlet having a second inner perimeter dimension that is smaller than the first inner perimeter dimension, the waveguide conduit and the inlet together defining a waveguide passage through which a physical waveguide is passable, which waveguide passage extends along a first axis;
      an outlet communicatively coupled to and aligned with the inlet, the outlet having a third inner perimeter dimension that is smaller than the second inner perimeter dimension, the outlet sized to permit egress of radiation from an output end of the waveguide, if any, positioned in the inlet;
      a handle having a frame and an angled opening, which angled opening extends through the frame along a second axis that is transverse to the first axis;
      a planar surface defining an interface between the inlet and the outlet; and
      a cantilevered distal extension that extends beyond the outlet, the cantilevered distal extension having a flat surface adjacent to the outlet.

5. The surgical device of claim 4, the distal tip further including a through-hole positioned adjacent to at least one of the inlet and the outlet.

\* \* \* \* \*